US009642819B2

(12) United States Patent
Nichols et al.

(10) Patent No.: US 9,642,819 B2
(45) Date of Patent: May 9, 2017

(54) LOW DOSAGE SEROTONIN 5-HT2A RECEPTOR AGONIST TO SUPPRESS INFLAMMATION

(75) Inventors: Charles D. Nichols, New Orleans, LA (US); Bangning Yu, New Orleans, LA (US)

(73) Assignee: BOARD OF SUPERVISORS OF LOUISIANA STATE UNIVERSITY AND AGRICULTURAL AND MECHANICAL, Baton Rouge, LA (US)

( * ) Notice: Subject to any disclaimer, the term of this patent is extended or adjusted under 35 U.S.C. 154(b) by 1061 days.

(21) Appl. No.: 12/501,105

(22) Filed: Jul. 10, 2009

(65) Prior Publication Data

US 2010/0016280 A1  Jan. 21, 2010

Related U.S. Application Data

(60) Provisional application No. 61/079,576, filed on Jul. 10, 2008.

(51) Int. Cl.
*A61K 31/397* (2006.01)
*A61K 31/138* (2006.01)
*A61K 31/48* (2006.01)

(52) U.S. Cl.
CPC .......... *A61K 31/138* (2013.01); *A61K 31/397* (2013.01); *A61K 31/48* (2013.01)

(58) Field of Classification Search
CPC ..... A61K 31/138; A61K 31/48; A61K 31/397
USPC .................................. 514/210
See application file for complete search history.

(56) References Cited

U.S. PATENT DOCUMENTS 6,664,286 B1 * 12/2003 May .................. A61K 31/00
                                                    514/392
7,244,843 B2 *  7/2007 Wacker et al. ........... 540/471

OTHER PUBLICATIONS

Macowiak et al. DOI, an agonist of 5-HT2A/2C serotonin receptor, alters the expression of cyclooxygenase-2 in the rat parietal complex, J Physiol Pharmacol., Sep. 2002;53(3):pp. 395-407.*
Nau et al (Am J Physiol Lung Cell Mol Physiol 308: L191-L198, 2015).*
Philip Reeves (Merck Manuals, http://www.merckmanuals.com/vet/pharmacology/pharmacology_introduction/drug_action_and_pharmacodynamics.html, accessed Apr. 7, 2015, published 2012).*
Drugs.com (http://www.drugs.com/sfx/etanercept-side-effects.html, accessed Oct. 5, 2015).*
Akiyoshi, T. et al., "Induction of indefinite survival of fully mismatched cardiac allografts and generation of regulatory cells by sarpogrelate hydrochloride," Transplantation, vol. 82, pp. 1051-105 (2006).

(Continued)

*Primary Examiner* — Savitha Rao
*Assistant Examiner* — Angela Brown-Pettigrew
(74) *Attorney, Agent, or Firm* — Clark & Elbing LLP

(57) ABSTRACT

The present invention is directed to a method for the treatment of an inflammatory disorder in a mammal, said method comprising administering to a mammal in need of such treatment a therapeutically effective amount of (R)-1-(2,5-dimethoxy-4-iodophenyl)-2-aminopropane ((R)-DOI) in a pharmaceutically acceptable carrier or salt thereof, wherein said inflammatory disorder is associated with a disease selected from asthma, rheumatoid arthritis, irritable bowel syndrome, and Crohn's disease.

7 Claims, 14 Drawing Sheets

(56) References Cited

OTHER PUBLICATIONS

Arzt, E. et al., "Serotonin inhibition of tumor necrosis factor-alpha synthesis by human monocytes," Life Sci, vol. 48, pp. 2557-2562 (1991).
Blankenberg, S. et al., "Adhesion molecules and atherosclerosis," Atherosclerosis, vol. 170, pp. 191-203 (2003).
Cloez-Tayarani, I. et al., "Differential effect of serotonin on cytokine production in lipopolysaccharide-stimulated human peripheral blood mononuclear cells: involvement of 5-hydroxytryptamine2A receptors," Int Immunol, vol. 15, pp. 233-240 (2003).
Crisafulli C. et al., "Effects of genetic and pharmacological inhibition of TNF-alpha in the regulation of inflammation in macrophases," Pharmacol. Res. (Epub May 18, 2009.).
Dunn, A.J. et al., Cytokines as mediators of depression: what can we learn from animal studies? Neurosci Biobehav Rev , vol. 29, pp. 891-909 (2005).
Hansson, G.K. et al., "Inflammation and atherosclerosis," Annu Rev Pathol, vol. 1, pp. 297-329 (2006).
Hughes, J.M. et al., "Human eosinophil-airway smooth muscle cell interactions," Mediators Inflamm, vol. 9, pp. 93-99 (2000).
Ito, T. et al., "Serotonin increases interleukin-6 synthesis in human vascular smooth muscle cells," Circulation, vol. 102, pp. 2522-2527 (2000).
Kim, Y.K. et al., "Imbalance between pro-inflammatory and anti-inflammatory cytokines in bipolar disorder," J Affect Disord, vol. 104, pp. 91-95 (2007).
Kubera. M. et al., "Effects of serotonin and serotonergic agonists and antagonists on the production of tumor necrosis factor alpha and interleukin-6," Psychiatry Res, vol. 134, pp. 251-258 (2005).
Marconi, A. et al., "Naftidrofuryl-driven regulation of endothelial ICAM-1 involves nitric oxide," Free Radic Biol Med, vol. 34, pp. 616-625 (2003).
Miller, K.J. et al., "Serotonin 5-HT2A receptor activation inhibits cytokine-stimulated inducible nitric oxide synthase in C6 glioma cells," Ann N Y Aced Sci, vol. 861, pp. 169-173 (1998).
Miller, K.J. et al., "Serotonin 5HT2A receptor activation inhibits inducible nitric oxide synthase activity in C6 glioma cells," Life Sci, vol. 61, pp. 1819-1827 (1997).
Nagatomo, T. et al., "Functions of 5-HT2A receptor and its antagonists in the cardiovascular system," Pharmacol Ther, vol. 104, pp. 59-81 (2004).
Nichols, D.E., "Hallucinogens," Pharmacol Ther, vol. 101, pp. 131-181 (2004).
Nichols, D.E. et al., "Serotonin Receptors," Chem Rev, vol. 108, pp. 1614-1641 (2008).
Popa, C. et al., "The role of TNF-alpha in chronic inflammatory conditions, intermediary metabolism, and cardiovascular risk," J Lipid Res, vol. 48, pp. 751-762 (2007).
Reimold, A.M., "TNFalpha as therapeutic target: new drugs, more applications," Curr Drug Targets Inflamm Allergy, vol. 1, pp. 377-392 (2002).
Roth, B.L. et al., "5-Hydroxytryptamine2 receptors coupled to phospholipase C in rat aorta: modulation of phosphoinositide turnover by phorbol ester," J Pharmacol Exp Ther, vol. 238, pp. 480-485 (1986).
Saetre, P. et al., "Inflammation-related genes up-regulated in schizophrenia brains," BMC Psychiatry, vol. 7, pp. 46 (2007).
Stefulj, J. et al., "mRNA expression of serotonin receptors in cells of the immune tissues of the rat," Brain Behav Immun, vol. 14, pp. 219-229 (2000).
Tracey, D. et al., "Tumor necrosis factor antagonist mechanisms of action: A comprehensive review," Pharmacol Ther. (2007).
Tweedie, D. et al., "TNF-alpha inhibition as a treatment strategy for neurodegenerative disorders: new drug candidates and targets," Curr Alzheimer Res, vol. 4, pp. 378-385 (2007).
Williams, R.O. et al., "Cytokine inhibitors in rheumatoid arthritis and other autoimmune diseases," Curr Opin Pharmacol, vol. 7, pp. 412-417 (2007).
Willins, D.L. et al., "Serotonin 5-HT2A receptors are expressed on pyramidal cells and interneurons in the rat cortex," Synapse, vol. 27, pp. 79 (1997).
Adner, Mikael et al., "An assay to evaluate the long-term effects of inflammatory mediators on murine airway smooth muscle: evidence that TNFα up-regulates $5-HT_{2A}$-mediated contraction," Brit. J. of Pharm., vol. 137, pp. 971-982 (2002).
Cazzola, M. et al., "5-HT Modifiers as a Potential Treatment of Asthma," TiPS, vol. 21, pp. 13-16 (2000).
Segura, P. et al., "Role of 5-HT21, 5-HT4 and 5-HT7 receptors in the antigen-induced airway hyperresponsiveness in guinea-pigs," Clin. & Exp. Allergy, vol. 40, pp. 328-338 (2009).
Alex, K.D. et al., "Pharmacologic Mechanisms of Serotonergic Regulation of Dopamine Neurotransmission," Pharmacology & Therapeutics, vol. 113, pp. 296-320 (2007).
Canal, Clint E. et al.,"Head-twitch Response in Rodents Induced by the Hallucinogen 2,5-dimethoxy-4-iodoamphetamine: A Comprehensive History, a Re-Evaluation of Mechanisms, and its Utility as a Model," Drug Test Anal., vol. 4, pp. 556-576 (2012).
Canal, Clinton E. et al., "Support for 5-HT2C Receptor Functional Selectivity in vivo Utilizing Structurally Diverse, Selective 5-HT2C Receptor Ligands and the 2,5-dimethoxy-4-iodoamphetamine Elicited Head-twitch Response Model," Neuropharmacology, vol. 70, pp. 112-121 (2013).
Halford, Jason C.G. et al., "$5-HT_{2C}$ Receptor Agonists and the Control of Appetite," *Appetite Control*, Handbook of Experimental Pharmacology, vol. 209, pp. 349-356 (2012).
Hannon, Jason et al., "Molecular Biology of 5-HT Receptors," Behav. Brain Res., vol. 195, pp. 198-213 (2008).
McKune, C.M. et al., "Characterization of the Serotonin Receptor Mediating Contraction in the Mouse Thoracic Aorta and Signal Pathway Coupling," The Journal of Pharm. and Exper. Therapeutics, vol. 297, No. 1, pp. 88-95 (2001).
Mitchell, Jane A. et al., "Selectivity of Nonsteroidal Antiinflammatory Drugs as Inhibitors of Constitutive and Inducible Cyclooxygenase," Proc. Natl. Acad. Sci., vol. 90, pp. 11693-11697 (1994).
Nakada, Marian T. et al., "Glucocorticoid Regulation of β-Adrenergic Receptors in 3T3-L1 Preadipocytes," Molecular Pharm., vol. 31, pp. 377-384 (1987).
Nau, Felix Jr. et al., "Serotonin 5-HT2A Receptor Activation Blocks TNF-α Mediated Inflammation In vivo," PLOS One, vol. 8, Iss. 10, pp. 1-8 (2013).
Nichols, Charles et al., "Serotonin 5-HT2A Receptor Activation Blocks TNF-Alpha Mediated Inflammation in vivo and Prevents Asthma," Serotonin Club Meeting, No. 30, p. 116 (2012).
Smith, Randy L. et al., "Discriminative Stimulus Properties of 1-(2,5-dimethoxy-4-iodophenyl)-2-aminopropane [(±)DOI] in C57BL/6J Mice," Psychopharmacology, vol. 166, pp. 61-68 (2003).
"Guidance for Industry: estimating the maximum safe starting dose in initial clinical trials for therapeutics in adult healthy volunteers," U.S. Department of Health and Human Services, Food and Drug Adminstration, and Center for Drug Evaluation and Research, Jul. 2005 (27 pages).
Pasparakis et al., "Immune and inflammatory responses in TNF alpha-deficient mice: a critical requirement for TNF alpha in the formation of primary B cell follicles, follicular dendritic cell networks and germinal centers, and in the maturation of the humoral immune response," J Exp Med. 184(4):1397-411 (1996).
Tobinick et al., "TNF-alpha modulation for treatment of Alzheimer's disease: A 6-month pilot study," MedGenMed. 8(2):25 (2006).
Tyring et al., "Etanercept and clinical outcomes, fatigue, and depression in psoriasis: double-blind placebo-controlled randomised phase III trial," Lancet. 367(9504):29-35 (2006).
Tobinick et al., "Rapid cognitive improvement in Alzheimer's disease following perispinal etanercept administration," J Neuroinflammation. 5:2 (2008) (10 pages).
Tobinick et al., "Selective TNF inhibition for chronic stroke and traumatic brain injury: an observational study involving 629 consecutive patients treated with perispinal etanercept," CNS Drugs. 26(12):1051-70 (2012).

(56) References Cited

OTHER PUBLICATIONS

Zaremba et al., "Early TNF-alpha levels correlate with ischaemic stroke severity," Acta Neurol Scand. 104(5):288-95 (2001).

* cited by examiner

LOW DOSAGE SEROTONIN 5-HT2A RECEPTOR AGONIST TO SUPPRESS INFLAMMATION

The benefit of the 10 Jul. 2008 filing date of U.S. provisional patent application 61/079,576 is claimed under 35 U.S.C. §119(e).

This invention was made with United States government support under Grant Nos. P20RR018766 and HL072889 awarded by the National Institutes of Health. The United States government has certain rights in this invention.

This invention relates to the use of serotonin 5-$HT_{2A}$ receptor agonists at low dosages no greater than about 5 nM, more preferably no greater about 1 nM, to treat tumor necrosis factor-alpha (TNF-α) related inflammation and inflammation-related diseases and conditions.

Serotonin 5-hydroxytryptamine (5-HT) receptors and agonists. Serotonin, 5-hydroxytryptamine (5-HT), is a small monoamine molecule primarily known for its role as a neurotransmitter. Within the brain, 5-HT modulates a variety of behaviors including cognition, mood, aggression, mating, feeding, and sleep (Nichols and Nichols, 2008). These behaviors are mediated through interactions at seven different receptor families (5-$HT_{1-7}$) comprised of fourteen distinct subtypes (Nichols and Nichols, 2008). Each of these are G-protein coupled receptors, with the exception of the 5-$HT_3$ receptor, which is a ligand-gated ion channel. Of all the serotonin receptors, the 5-$HT_{2A}$ receptor, which is known to primarily couple to the Gαq effector pathway (Roth et al., 1986), has been the one most closely linked to complex behaviors. There is a high level of expression of 5-$HT_{2A}$ receptors within the frontal cortex, with significant localization to the apical dendrites of cortical pyramidal cells (Willins et al., 1997), and further expression at lower levels throughout the brain (Nichols and Nichols, 2008). These receptors have been shown to participate in processes such as cognition and working memory, have been implicated in affective disorders such as schizophrenia, and have been shown to mediate the primary effects of hallucinogenic drugs (Nichols, 2004).

In addition, many peripheral tissues express 5-$HT_{2A}$ receptors. Within the vasculature, 5-$HT_{2A}$ receptors are known to modulate vasoconstriction (Nagatomo et al., 2004). Its role in other tissues such as mesangial cells of the kidney, fibroblasts, liver, and lymphocytes remains less defined, but has been linked to cellular proliferation and differentiation.

The presence of 5-$HT_{2A}$ receptor mRNA (along with the mRNAs of other serotonin receptor subtypes) has been found in tissues involved in the immune response (Stefulj et al., 2000). The role of 5-$HT_{2A}$ receptors in inflammatory processes, however, is unclear, with only a few published and inconsistent reports. For example, blockage of 5-$HT_{2A}$ receptor function with the selective antagonist sarpogrelate has been reported to decrease expression of proinflammatory markers (Marconi et al., 2003; Akiyoshi et al., 2006), and conversely reported to increased expression of proinflammatory markers (Ito et al., 2000). Using extremely high non-pharmacologically relevant drug doses (lowest dose was 25 μM), a 5-$HT_2$ receptor specific agonist, 1-(2,5-dimethoxy-4-iodophenyl)-2-aminopropane (DOI; the racemic form), was alleged to repress IL-1β expression and production of TNF-α due to lipopolysaccharide stimulation through 5-$HT_{2A}$ receptor activation (Cloez-Tayarani et al., 2003).

Two other studies reported that DOI acting at 5-$HT_2$ receptors partially blocked LPS and cytokine stimulated nitrite accumulation using a cocktail of TNF-α and TNF-γ in C6 glioma cells, and reported an IC50 value of 8±3 nM. (Miller et al., 1997; Miller and Gonzalez, 1998). In earlier reports, the synthesis of TNF-α in response to LPS stimulation of toll-like receptors was reported to be inhibited by 5-HT through 5-$HT_2$ receptors in monocytes (Arzt et al., 1991). The use of ketanserin as the antagonist to block 5-$HT_2$ receptor activation in many of these studies to indicate 5-$HT_{2A}$ receptor involvement is problematic, since ketanserin has only weak selectivity (~20-fold) for 5-$HT_{2A}$ receptors over 5-$HT_{2C}$ receptors, and has a high affinity for $α_1$-adrenergic receptors, and significantly, is equipotent at blocking histamine $H_1$ receptors, which are known to regulate inflammatory processes. Ketanserin cannot be used to discriminate reliably between the effects of agonists acting at 5-$HT_{2A}$ or 5-$HT_{2C}$ receptors.

The presence of serotonin itself has been demonstrated to be necessary for expression of the inflammatory markers IL-6 and TNF-α, with lower serotonin levels inducing, and higher levels decreasing expression of these markers (Kubera et al., 2005). This inverted-U shaped response clearly indicates that in vivo serotonin plays an important role in modulating molecular components of the inflammatory process. The identity of the serotonin receptor mediating these processes has not been reliably established.

Primary cultures of rat aortic smooth muscle (RASM) are a well established system to study inflammatory processes. Aortic smooth muscle cells normally form the media of the aorta, and serve to provide and regulate vascular tone of the artery. Significantly, the pathophysiological status of vascular smooth muscle cells is a crucial determinant of vascular disease (Hansson et al., 2006). During the development of atherosclerosis, which is believed to have a major inflammatory component, levels of cytokines such as TNF-α are elevated, leading to increased expression of genes and proteins, e.g., ICAM-1 and VCAM-1, in aortic smooth muscle (Blankenberg et al., 2003; Hansson et al., 2006). ICAM-1 (CD 54) belongs to the immunoglobulin (IgG) superfamily and is expressed in many cell types, including vascular endothelial cells, epithelial cells, fibroblasts, and macrophages (Hughes et al., 2000). Cytokine-mediated increased levels of intracellular adhesion molecules like ICAM-1 in aortic smooth muscle serve as an important component of atherosclerotic plaque formation.

The Immune Response System in Mammals. There are two immune response systems in mammals. One is an innate immunity, and is the system whereby the organism recognizes acute pathogens like invading bacteria. There are specific receptors on cells within the organism known as "Toll-like receptors" (TLRs) that are pattern recognition receptors that recognize antigens present on pathogenic micro-organisms. When a cell encounters these pathogens, TLRs are activated by antigens on the pathogen. This activation induces an inflammatory response which partially involves the activation of Nuclear Factor k-B (NFkB), and transcription of proinflammatory genes including cytokines and cell adhesion molecules. Activation of TLRs, primarily on monocytes and macrophage cells, with bacterially derived agents like lipopolysaccharide (LPS) induces the production and release of large amounts of tumor necrosis factor-alpha (TNF-α) from the monocyte and macrophage cells.

Tumour necrosis factor-alpha (TNF-α) is an inflammatory cytokine produced by circulating monocytes and resident macrophages during acute inflammation. Macrophages are, upon stimulation, the main producers of TNF-α as well as they are also the primary infiltrating cells at the site of inflammation. After TNF-α is released from these cells, one action is to bind to its specific receptor proteins (TNFR1 and TNFR2) present on the surface of almost every cell type. TNF-α receptors (TNFRs) are members of a different class of receptor proteins than TLRs, and recognize the endogenously produced cytokine TNF-α. Whereas TNF-α is predominantly produced and released from circulating monocytes and resident macrophages at the site of infection or injury, TNF-α receptors are expressed in nearly every cell. Through a view different signaling pathway from that used by TLR receptors, a pathway that involves completely different proteins, TNF-α receptor stimulation can lead to activation and nuclear translocation of NF-kB, and transcription of proinflammatory genes including cytokines and cell adhesion molecules.

When TNF-α binds to its specific receptor, a diverse range of signal transduction events are initiated from the activated receptor that lead to cellular responses, which include responses like inflammation, necrosis, apoptosis, cell survival, and cell migration. During acute inflammation. TNF-α overproduction is crucial in the induction of inflammatory genes, cell death, endothelial up-regulation, and in the recruitment and activation of immune cells. TNF is a "master" cytokine in inflammatory diseases. Anti-TNF agents have been very effective in chronic inflammatory conditions in patients such as rheumatoid arthritis, even in the absence of other anti-cytokine agents. (Crisafulli et al 2009).

Whereas production and release of TNF-α from monocytes and macrophages can be induced by TLRs during the process of infection, there are many other mechanisms independent of TLRs that can regulate TNF-α concentrations. For example, oxidative stress in cells can lead to elevated levels of TNF-α, as well as direct activation of NFkB, to produce inflammation. Oxidative stress can be caused by pathological conditions that include diabetes, metabolic disorder, and neurological disorders, and the resulting increase in inflammation can contribute to the development and progression of diseases like atherosclerosis, arthritis, and asthma.

TNF-α and TNF-α receptor-mediated inflammatory pathways have been strongly implicated in a number of diseases including atherosclerosis, rheumatoid arthritis, psoriasis, type II diabetes, irritable bowel syndrome, Crohn's disease, and septicemia (e.g., Reimold, 2002; Popa et al., 2007; Williams et al., 2007). Significantly, TNF-α and other cytokine induced inflammatory pathways also have been linked to psychiatric conditions such as depression and bipolar disorder (Dunn et al., 2005; Kim et al., 2007), as well as schizophrenia (Saetre et al., 2007), and neurodegenerative diseases like Alzheimer's and Parkinson's disease and stroke (Tweedie et al., 2007). As such, inhibitors of TNF-α-mediated proinflammatory pathways represent potential therapeutics for each of these conditions. Currently, the only available therapeutic inhibitors of TNF-α pathways are monoclonal antibodies against TNF-α (infliximab and adalimumab) and soluble TNF-α receptor (etanercept), and the development of small molecules for this purpose is highly desirable (Tracey et al., 2007).

Potential therapeutic strategies aimed at blocking TNF-α synthesis and release would primarily target the monocytes and macrophage cells. In contrast, therapeutic strategies that are aimed at blocking the TNF-α receptor-induced signal transduction pathways by 5-HT$_{2A}$ receptor activity would aim at any tissue cell expressing TNF-α receptors, which include most cell types in the body (e.g. smooth muscle cells, neurons, skin cells).

DISCLOSURE OF INVENTION

We have shown that activation of 5-HT$_{2A}$ receptors using agonists at concentrations no greater than 5 nm, more preferably no greater than 1 nM, potently inhibits TNF-α-induced inflammation in multiple cell types, including rat aortic smooth muscle cells, human neuroblastoma cells, rat glioma cells, rat aortic epithelial cells, and rat bronchoaveolar macrophage cells. We have shown that 5-HT$_{2A}$ receptor stimulation with the agonist (R)-DOI rapidly inhibits a variety of proinflammatory markers mediated by TNF-α acting at its receptors, including ICAM-1, VCAM-1, and IL-6 gene expression, NOS activity, and nuclear translocation of NF-κB, with IC$_{50}$ values of only 10-20 pM. Significantly, proinflammatory markers also can be inhibited by (R)-DOI many hours after treatment with TNF-α. With the exception of a few natural toxins, no current drugs or small molecule therapeutics demonstrate a comparable potency for any physiological effect. TNF-α-mediated inflammatory pathways have been strongly implicated in a number of diseases, including atherosclerosis, rheumatoid arthritis, asthma, psoriasis, type II diabetes, depression, schizophrenia, and Alzheimer's disease. Our results indicate that activation of 5-HT$_{2A}$ receptors represents an extraordinarily potent, potential therapeutic avenue for the treatment of disorders involving TNF-α-mediated inflammation. Importantly, because (R)-DOI can significantly inhibit the effects of TNF-α many hours after the administration of TNF-α, potential therapies could be aimed not only at preventing inflammation, but also treating inflammatory injury that has already occurred or is ongoing.

Figure 1A:
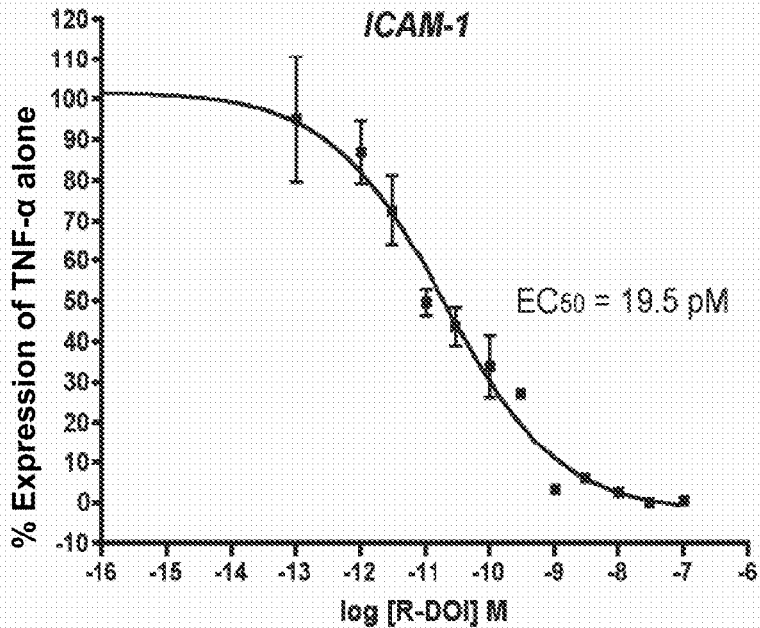
FIG. 1A illustrates the effect of 5-HT$_{2A}$ receptor activation with the agonist (R)-DOI on the expression of ICAM-1 in primary rat aortic smooth muscle cells (passage 4). The Y-axis represents percent of TNF-α control induction for the dose of (R)-DOI indicated on the X-axis. The IC$_{50}$ for proinflammatory gene expression inhibition for ICAM-1 is 19.5 pM.

Current anti-inflammatory agents directly target other pathways, for example, the inhibition of prostaglandin synthesis or production of cytokines. Most published reports probing the role of serotonin 5-HT$_2$ receptors in inflammation have primarily focused on the use of antagonists (blockers) as anti-inflammatory agents. We have shown that the use of serotonin 5-HT$_{2A}$ receptor agonists (activators) at extremely low concentration, e.g., (R)-DOI, inhibits inflammatory marker gene expression with a potency at least 100 times greater than any current drug on the market. This allows for the treatment of inflammatory diseases and conditions with small doses of drug, which would decrease the likelihood of undesirable side effects. At the doses of drug found effective in this technology, inflammation processes could be targeted very specifically with little to no undesirable side effects due to off target receptor activation.

We have discovered that activation of 5-HT$_{2A}$ receptors in primary aortic smooth muscle cells provides a previously unknown and extremely potent inhibition of TNF-α-mediated inflammation. 5-HT$_{2A}$ receptor stimulation with the agonist (R)-DOI rapidly inhibits a variety of proinflammatory markers mediated by TNF-α acting at its receptors, including ICAM-1, VCAM-1, and IL-6 gene expression, NOS activity, and nuclear translocation of NF-κB, with IC$_{50}$ values of only 10-20 pM. Significantly, proinflammatory markers also can be inhibited by (R)-DOI many hours after treatment with TNF-α. With the exception of a few natural toxins, no current drugs or small molecule therapeutics demonstrate a comparable potency for any physiological effect. TNF-α-mediated inflammatory pathways have been strongly implicated in a number of diseases, including atherosclerosis, asthma, rheumatoid arthritis, psoriasis, type II diabetes, depression, schizophrenia, and Alzheimer's disease. Our results indicate that activation of 5-HT$_{2A}$ receptors represents an extraordinarily potent, potential therapeutic avenue for the treatment of disorders involving TNF-α-mediated inflammation. Importantly, because (R)-DOI can significantly inhibit the effects of TNF-α many hours after the administration of TNF-α, potential therapies could be aimed not only at preventing inflammation, but also treating inflammatory injury that has already occurred or is ongoing.

EXAMPLE 1

Material and Methods

Reagents and Chemicals. Standard cell culture media (M-199) was provided by the Molecular and Cell core at Louisiana State University Health Science Center in New Orleans (LSUHSC-NO). Supplements to the media were from Invitrogen (Carlsbad, Calif.). TNF-α (rat and human) was purchased from Peprotech, Inc. (Rocky Hill, N.J.). The 5-HT$_{2C}$ receptor antagonist RS102221 (8-[5-(2,4-Dimethoxy-5-(4-trifluoromethylphenylsulphonamido)phenyl-5-oxopentyl]-1,3,8-triazaspiro[4.5]decane-2,4-dione hydrochloride), HT$_{2B}$ receptor antagonist SB204741 (N-(1-Methyl-1H-indolyl-5-yl)-N"-(3-methyl-5-isothiazolyl)urea, PKC inhibitor Gö6976 (5,6,7,13-Tetrahydro-13-methyl-5-oxo-12H-indolo[2,3-a]pyrrolo[3,4-c]carbazole-12-propanenitrile), and PKC inhibitor chelerythrine (1,2-Dimethoxy-12-methyl[1,3]benzodioxolo[5,6-c]phenanthridinium chloride) were purchased from Tocris (Ellisville, Mo.). PKC activator PMA (Phorbol 12-myristate 13-acetate), and PKA inhibitor fragment 6-22 amide (F-22) were purchased from Sigma (St. Louis, Mo.). (R)-DOI ((R)-1-(2, 5-dimethoxy-4-iodophenyl)-2-aminopropane) (greater than 95% R enantiomer), LA-SS-Az (2'S,4'S)-(+)-9,10-Didehydro-6-methylergoline-8β-(trans-2,4-dimethylazetidide), 2C-BCB (4-Bromo-3,6-dimethoxybenzocyclobuten-1-yl) methylamine, and MDL100907 (R(+)-a-(2,3-dimeth-oxyphenyl)-1-[2-(4-fluorophenylethyl)]-4-pipeddine-methanol) were obtained from Purdue University. Lysergic acid diethylamide (LSD) was provided by the National Institute on Drug Abuse.

RASM cells and treatment. Rat aortic smooth muscle (RASM) cells were isolated from adult 180 g male Sprague-Dawley rats and provided by the Cell and Molecular Core Facility in the Department of Pharmacology at LSUHSC-NO. Isolated RASM cells were grown in M-199 media containing 10% fetal bovine serum (Gibco), 100 units/mL penicillin, and 100 g/mL streptomycin, and incubated at 37° C. in 5% CO$_2$. Cells for all assays were used between passages 3 and 5. Prior to treatments, cells were grown in M-199 media with 10% fetal bovine serum (FBS) until 30-50% confluent. For most assays, cells were treated with (R)-DOI, or other drugs as indicated, at specific concentrations for 24 hours, followed by TNF-α (10 ng/ml) and (R)-DOI at the same pretreatment concentrations in fresh M-199 media. After another 24 hours, the cells were scraped, pelleted, and processed for RNA. Pretreatment and treatment times varied with assays as indicated in the results section.

RNA isolation and Quantitative Realtime-PCR. RNA was extracted from cells using Illustra RNAspin Mini kits from GE Healthcare Life Sciences (Piscataway, N.J.) following protocols supplied by the manufacturer. First strand cDNA was generated using the ImProm-II cDNA synthesis kit (Promega) following the manufacturers protocols. Q-RT-PCR was performed using the ProbeLibrary system from Roche (Indianapolis, Ind.) in combination with the HotStart-IT probe qpcr master mix from USB Biological (Cleveland, Ohio) following manufactures protocols.

The sequences of primers used are: 5-HT$_{2A}$R (5-hydroxytryptamine 2A receptor): forward primer 5'-TGATGT-CACTTGCCATAGCTG-3' (SEQ ID NO: 1), reverse primer, 5'TCGCACAGAGCTTGCTAGG-3' (SEQ ID NO: 2); ICAM-1 (intracellular adhesion molecule 1): forward primer, 5'-TTCTGCCACCATCACTGTGT-3' (SEQ ID NO: 3, reverse primer, 5'-AGCGCAGGATGAGGTTCTT-3' (SEQ ID NO: 4); VCAM-1 (vascular adhesion molecule 1): forward primer, 5'-CAAATGGAGTCTGAACCCAAA-3' (SEQ ID NO: 5), reverse primer, 5'-GGTTCTTTCGGAG-CAACG-3' (SEQ ID NO: 6); IL-6 (interleukin-6): forward primer, 5'-CCTGGAGTTTGTGAA GAACAACT-3' (SEQ ID NO: 7), reverse primer, 5'-GGAAGTTGGGGTAG-GAAGGA-3' (SEQ ID NO: 8); and cyclophillin B (control amplicon): forward primer, 5'-ACGTGGTTTTCG-GCAAAGT-3' (SEQ ID NO: 9), reverse primer, 5'-CTTG-GTGTTCTCCACCTTCC-3' (SEQ ID NO: 10). Primers were synthesized by IDT (Coralville, Iowa). ProbeLibrary probes from Roche were: U3, U74, U13, U106, U79 for 5-HT$_{2A}$R, ICAM-1, VCAM-1, IL-6, and cyclophillin B, respectively. Quantitative determination of gene expression levels using a 2-step cycling protocol was performed on a MyIQ-5 Cycler (Bio-Rad, Hercules Calif.). Relative gene expression levels were calculated using the $2^{[-\Delta\Delta C(T)]}$ method. Levels of all targets from the test samples were normalized to rat cyclophillin B expression.

Nitric Oxide Synthetase (NOS) Activity. NOS activity was determined by detection of nitrite levels in the cell culture medium following (R)-DOI/TNF-α treatments utilizing the Nitrate Detection kit from Assay Designs (Ann Arbor, Mich.) following the manufacturers protocols. Absorbances were detected at 539 nm on a Molecular Dynamics SpectraMax M2 plate reader.

Nuclear Translocation of p65. RASM cells were grown in M-199 medium+10% FBS until 50% confluent in 8 well chamber slides. Cells were treated with 1 nM (R)-DOI for various times as indicated, and TNF-α (10 ng/ml; tumor necrosis factor alpha) added. Thirty minutes after TNF-α treatment, cells were fixed and processed with rabbit anti p65 primary and Alexafluor 488-conjugated goat secondary antibodies as described in Zerfaoui et al. (2008) (Zerfaoui et al., 2008). Fluorescent signal was visualized on a Leica DMRA2 fluorescent microscope.

EXAMPLE 2

Figure 1B:
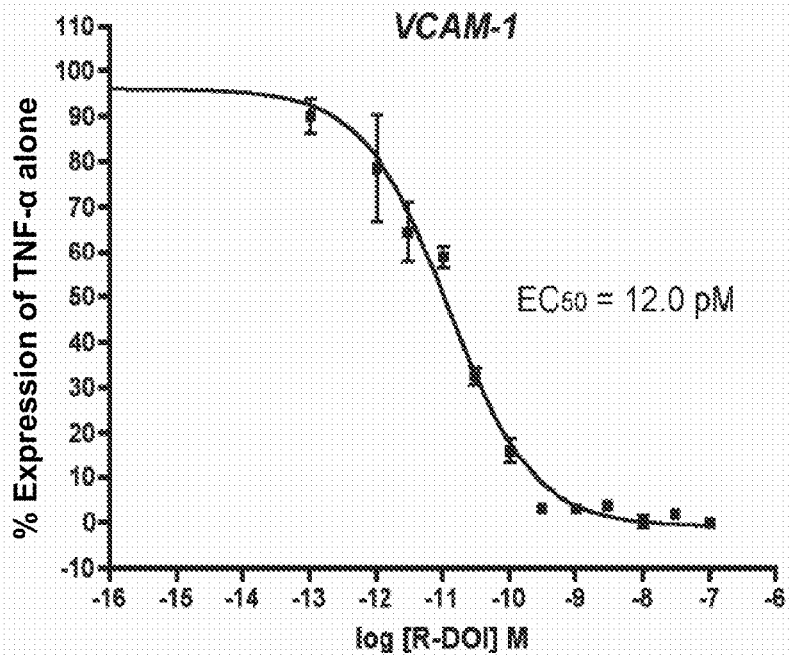
FIG. 1B illustrates the effect of 5-HT$_{2A}$ receptor activation with the agonist (R)-DOI on the expression of VCAM-1 in primary rat aortic smooth muscle cells (passage 4). The Y-axis represents percent of TNF-α control induction for the dose of (R)-DOI indicated on the X-axis. The IC$_{50}$ for proinflammatory gene expression inhibition for VCAM-1 is 12.0 pM.
Figure 1C:
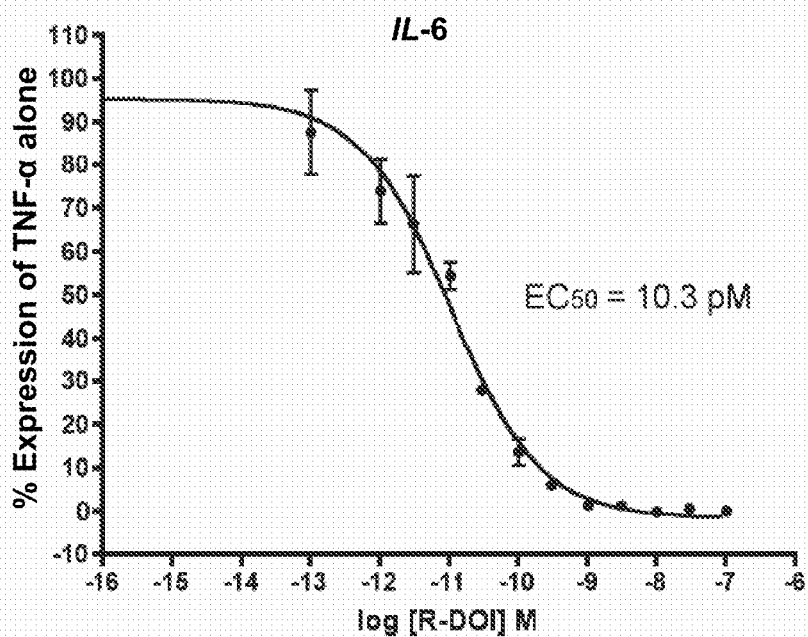
FIG. 1C illustrates the effect of 5-HT$_{2A}$ receptor activation with the agonist (R)-DOI on the expression of IL-6 in primary rat aortic smooth muscle cells (passage 4). The Y-axis represents percent of TNF-α control induction for the dose of (R)-DOI indicated on the X-axis. The IC$_{50}$ for proinflammatory gene expression inhibition for IL-6 is 10.3 pM.

(R)-DOI Super-Potently Inhibits TNF-α Induced Expression of Proinflammatory Genes Primary rat aortic smooth muscle (RASM) cells were verified to express $5\text{-HT}_{2A}$ mRNA by QRT-PCR using primer sequences and probe as described in the methods section of Example 1 (data not shown). To examine the effects of $5\text{-HT}_{2A}$ receptor activation on TNF-α mediated proinflammatory gene expression, RASM cells were pre-treated with (R)-DOI, a selective $5\text{-HT}_2$ receptor agonist, as described above. Dose-response curves were determined for the effects on ICAM-1, VCAM-1, and IL-6 gene expression for twelve different concentrations of (R)-DOI ranging from 0.1 pM to 100 nM, with each experiment repeated in triplicate. The results are shown in FIGS. 1A, 1B, and 1C. In FIGS. 1A-1C, the Y-axis represents a percent of TNF-α for the dose of (R)-DOI indicated on the X-axis. The $IC_{50}$ for proinflammatory gene expression inhibition is between 10-20 pM for all three (ICAM-1=19.5 pM; VCAM-1=12.0 pM; IL-6=10.3 pM). This indicates that (R)-DOI is a surprisingly super-potent inhibitor of each of these genes with an $IC_{50}$ in the picomolar range.

The experiments were repeated with fresh dilutions of drug and different batches of RASM cells, with the same results: a super-potent effect. TNF-α alone consistently increased baseline mRNA expression of these genes eight-ten fold, whereas (R)-DOI had no effect by itself (Data not shown).

Figure 1D:
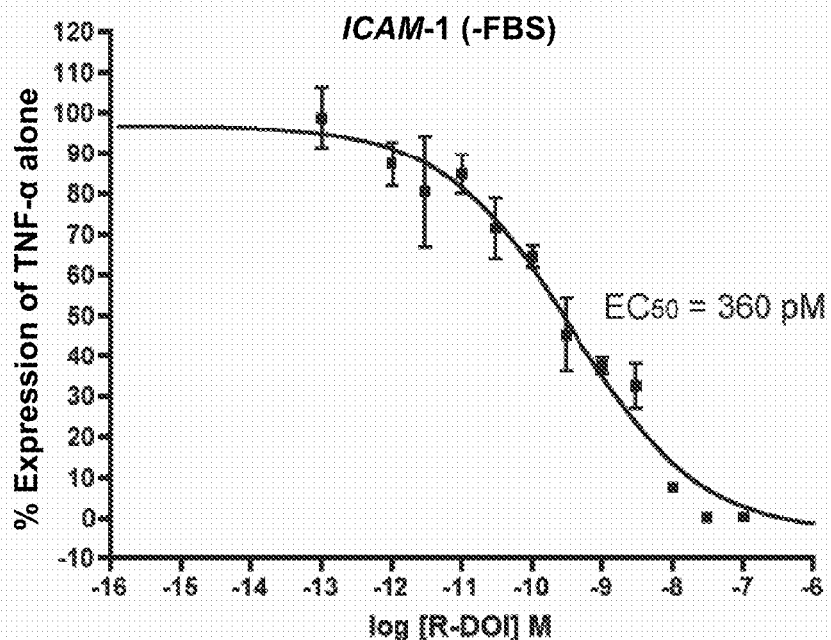
FIG. 1D illustrates the effect of 5-HT$_{2A}$ receptor activation with the agonist (R)-DOI on the expression of ICAM-1 in primary rat aortic smooth muscle cells (passage 4) in serum-free media. The Y-axis represents percent of TNF-α control induction for the dose of (R)-DOI indicated on the X-axis. The IC$_{50}$ for proinflammatory gene expression inhibition for ICAM-1 in serum-free media is 360 pM.

Because complete media with FBS contains serotonin, which may affect the results, the effects of (R)-DOI on TNF-α-induced ICAM1 expression were examined in cells serum starved for 8 hours. FIG. 1D shows an ICAM1 expression dose response curve in serum-free media. The $IC_{50}$ increased slightly to 360 pM over that seen in the experiments with FBS. All experiments were performed in RASM cells at passage 4. (FIG. 1D).

Non-steroidal anti-inflammatories (NSAIDS) typically have $IC_{50}$ values in the micromolar range for their targets, whereas steroidal anti-inflammatory drugs typically have $IC_{50}$ values in the low nanomolar range (Huntjens et al., 2005). The $IC_{50}$ values in the low picomolar range for (R)-DOI to block proinflammatory markers show that (R)-DOI activation of $5\text{-HT}_{2A}$ receptors is ~300-fold more potent than the more effective current anti-inflamatory agents. With the exception of a few natural toxins (e.g. botulinum toxin), no current drugs or small molecule therapeutics demonstrate a comparable potency for any physiological effect.

EXAMPLE 3

Inhibition of Proinflammatory Markers Mediated Through $5\text{-HT}_{2A}$ Receptor Activation Because (R)-DOI is an agonist at all three $5\text{-HT}_2$ receptor isoforms, receptor selective antagonists were selected to determine which receptor was mediating the (R)-DOI effect. RASM cells were treated with a control solution (Control), TNF-α alone (TNF-α), (R)-DOI alone (DOI), pretreatment with (R)-DOI (1 nM) prior to TNF-α (DOI+TNF), pretreatment with the $5\text{-HT}_{2A}$ receptor selective antagonist M100907 (100 nM) 30 minutes prior to (R)-DOI and TNF-α (M+D+T), pretreatment with 100 nM of the $5\text{-HT}_{2B}$ receptor selective antagonist SB204741 prior to (R)-DOI and TNF-α (S+D+T), and pretreatment with 100 nM of the $5\text{-HT}_{2B}$ receptor selective antagonist SB204741 prior to (R)-DOI and TNF-α (S+D+T).

Figure 2A:
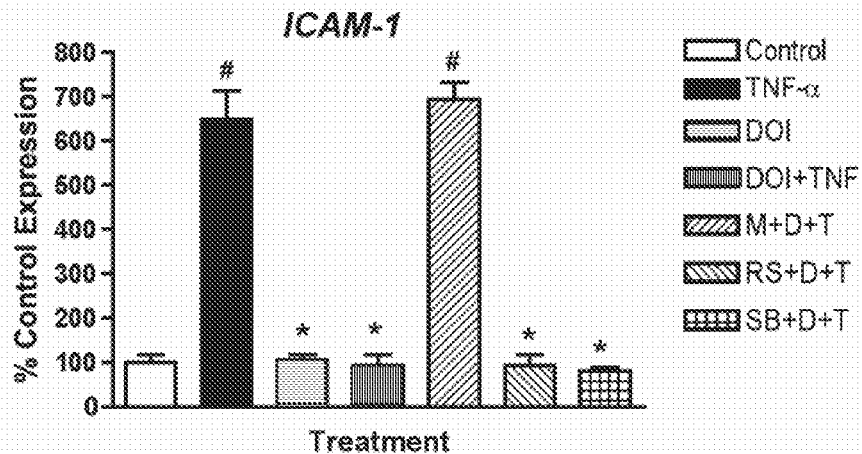
FIG. 2A illustrates the effect of 5-HT$_{2A}$ receptor activation on the expression of ICAM-1 in primary rat aortic smooth muscle cells (passage 4) under various conditions: control, TNF-α treatment alone (10 ng/ml) (TNF), pre-treatment with (R)-DOI (1 nM) prior to TNF-α (DOI+TNF), pretreatment with the 5-HT$_{2A}$ receptor selective antagonist M100907 (100 nM) 30 minutes prior to (R)-DOI (M+D+T), pretreatment with 100 nM of the 5-HT$_{2B}$ receptor selective antagonist SB204741 30 minutes prior to (R)-DOI (S+D+T), or pretreatment with 100 nM of the 5-HT$_{2C}$ receptor selective antagonist RS102221 30 minutes prior to (R)-DOI (R+D+T). (#p<0.01 vs control; *p<0.01 vs TNF-α alone; ANOVA with Tukey post hoc)
Figure 2B:
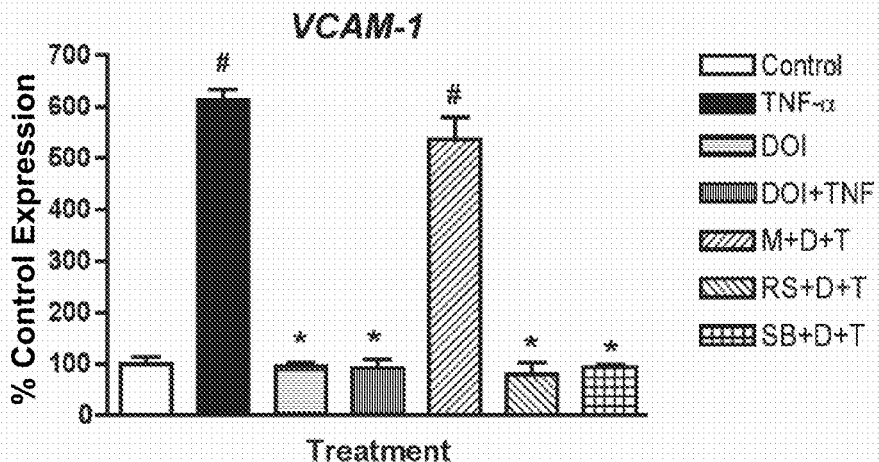
FIG. 2B illustrates the effect of 5-HT$_{2A}$ receptor activation on the expression of VCAM-1 in primary rat aortic smooth muscle cells (passage 4) under various conditions: control, TNF-α treatment alone (10 ng/ml) (TNF), pre-treatment with (R)-DOI (1 nM) prior to TNF-α (DOI+TNF), pretreatment with the 5-HT$_{2A}$ receptor selective antagonist M100907 (100 nM) 30 minutes prior to (R)-DOI (M+D+T), pretreatment with 100 nM of the 5-HT$_{2B}$ receptor selective antagonist SB204741 30 minutes prior to (R)-DOI (S+D+T), or pretreatment with 100 nM of the 5-HT$_{2C}$ receptor selective antagonist RS102221 30 minutes prior to (R)-DOI (R+D+T). (#p<0.01 vs control; *p<0.01 vs TNF-α alone; ANOVA with Tukey post hoc)
Figure 2C:
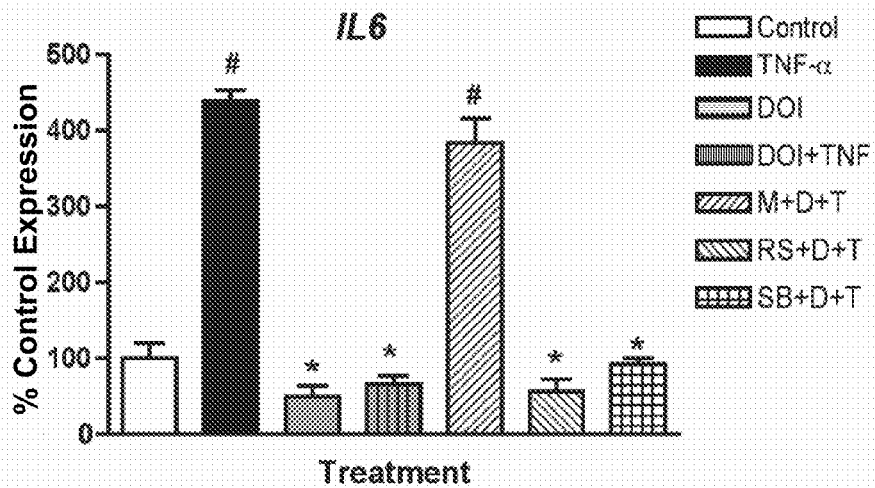
FIG. 2C illustrates the effect of 5-HT$_{2A}$ receptor activation on the expression of IL-6 in primary rat aortic smooth muscle cells (passage 4) under various conditions: control, TNF-α treatment alone (10 ng/ml) (TNF), pre-treatment with (R)-DOI (1 nM) prior to TNF-α (DOI+TNF), pretreatment with the 5-HT$_{2A}$ receptor selective antagonist M100907 (100 nM) 30 minutes prior to (R)-DOI (M+D+T), pretreatment with 100 nM of the 5-HT$_{2B}$ receptor selective antagonist SB204741 30 minutes prior to (R)-DOI (S+D+T), or pretreatment with 100 nM of the 5-HT$_{2C}$ receptor selective antagonist RS102221 30 minutes prior to (R)-DOI (R+D+T). (#p<0.01 vs control; *p<0.01 vs TNF-α alone; ANOVA with Tukey post hoc)

The results are shown in FIGS. 2A, 2B, and 2C for the induced expression of ICAM-1, VCAM-1, and IL-6, respectively. TNF-α treatment alone (10 ng/ml) (TNF-α) induced expression of ICAM-1, VCAM-1, and IL-6. (R)-DOI at 1 nM alone had no effect on expression of any of the three genes (DOI). Pre-treatment with (R)-DOI (1 nM) prior to TNF-α completely blocked the increase in proinflammatory gene expression by TNF-α (DOI+TNF). Pretreatment with the $5\text{-HT}_{2A}$ receptor selective antagonist M100907 (100 nM) 30 minutes prior to (R)-DOI blocked the effects of (R)-DOI (M+D+T). Pretreatment with 100 nM of the $5\text{-HT}_{2B}$ receptor selective antagonist SB204741 (S+D+T), or the $5\text{-HT}_{2C}$ receptor selective antagonist RS102221 (R+D+T) did not block the effects of (R)-DOI. In FIGS. 2A, 2B, and 2C, the symbols represent the following: #=p<0.01 vs control; *=p<0.01 vs TNF-α alone as analyzed with an ANOVA with Tukey post hoc)

As shown above, pretreatment of the cells with 100 nM of either the $5\text{-HT}_{2C}$ receptor selective antagonist RS102221, or the $5\text{-HT}_{2B}$ receptor selective antagonist SB204741 for 30 minutes prior to the addition of 1 nM (R)-DOI (a dose that completely inhibits TNF-α induced proinflammatory gene expression) had no effect. Pretreatment with 100 nM of the $5\text{-HT}_{2A}$ receptor selective antagonist MDL100907 for 30 minutes, however, completely blocked the inhibitory effects of 1 nM (R)-DOI on TNF-α mediated ICAM-1, VCAM-1, and IL-6 gene expression changes (FIGS. 2A, 2B, and 2C, respectively), indicating that the effects of (R)-DOI on these processes are being mediated exclusively through the $5\text{-HT}_{2A}$ receptors.

EXAMPLE 4

Additional $5\text{-HT}_{2A}$ Receptor Agonists Inhibit Proinflammatory Marker Expression To examine if these effects were exclusive for (R)-DOI acting at $5\text{-HT}_{2A}$ receptors, other $5\text{-HT}_{2A}$ agonists were tested for ability to inhibit proinflammatory marker expression. These included an additional phenethylamine, 4-Bromo-3,6-dimethoxybenzocyclobuten-1-yl) methylamine (2C-BCB), and two indolealkylamines, (2'S,4'S)-(+)-9,10-Didehydro-6-methylergoline-8β-(trans-2,4-dimethylazetidide) (LA-SS-Az) and lysergic acid diethylamide (LSD). All three have high affinity for rat $5\text{-HT}_{2A}$ receptors (Ki of 2C-BCB=0.73 nM; LA-SS-Az=8.3 nM; LSD=3.5 nM) as well as high potency for activating PI turnover ($EC_{50}$ of 2C-BCB=36 nM; LA-SS-Az=19 nM; LSD=15 nM) (Nichols et al., 2002; McLean et al., 2006).

Figure 3:
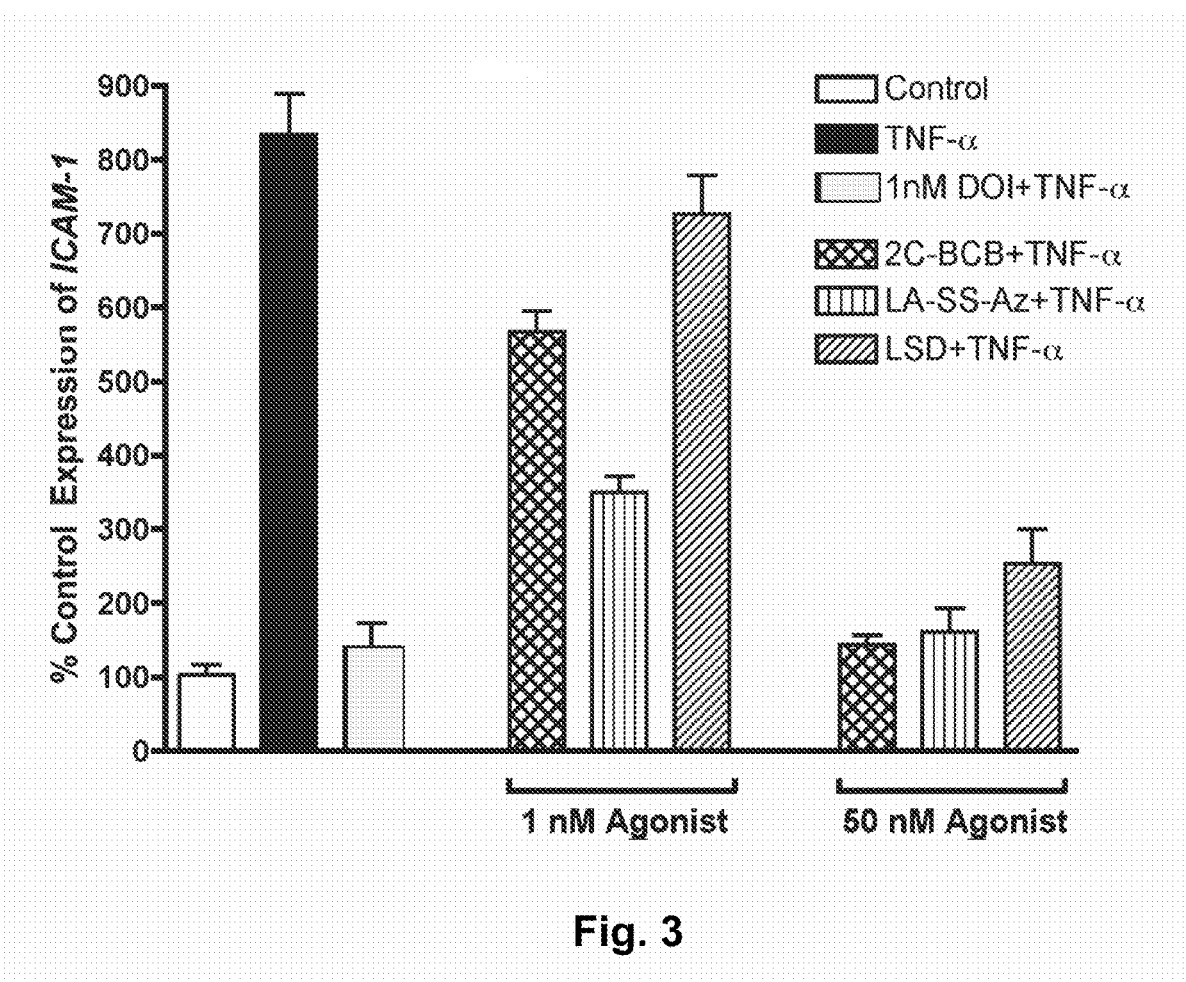
FIG. 3 illustrates the effect of 5-HT$_{2A}$ receptor activation on the expression o ICAM-1 in primary rat aortic smooth muscle cells (passage 4) under various conditions: control; TNF-α treatment alone (10 ng/ml) (TNF-α); pretreatment with (R)-DOI (1 nM, a 5-HT$_{2A}$ receptor agonist) prior to TNF-α (DOI+TNF-α), pretreatment with the phenethylamine 2C-BCB (1 nM and 50 nM, a 5-HT$_{2A}$ receptor agonist) prior to TNF-α (2C-BCB+TNF-α); pretreatment with the indolealkylamine LA-SS-Az (1 nM and 50 nM, a 5-HT$_{2A}$ receptor agonist) prior to TNF-α (LA-SS-Az+TNF-α); and pretreatment with the indolealkylamine LSD (1 nM and 50 nM, a 5-HT$_{2A}$ receptor agonist) prior to TNF-α (LSD+TNF-α).

The phenethylamine 2C-BCB, and the indolealkylamines LA-SS-Az and LSD, were tested for their ability to block TNF-α-mediated increases in proinflammatory gene expression at both 1 nM and 50 nM concentrations. The results with ICAM1 are shown in FIG. 3. Results for VCAM1 and IL6 were identical (Data not shown). Whereas (R)-DOI blocked gene expression at 1 nM, 2C-BCB and LSD only had weak to moderate effects at 1 nM. LA-SS-Az was moderately effective at this dose and blocked about 50% of induced gene expression. At the higher concentration of 50 nM, 2C-BCB and LA-SS-Az effectively blocked TNF-α induced gene expression. However, LSD only blocked about 85% of the effect.

Thus, the effects at both 1 nM and 50 nM pretreatment on gene expression of other $5\text{-HT}_{2A}$ receptor ligands show that they also may have potent effects (FIG. 3). Whereas the effects are potent (predicted $IC_{50}$ values in the low nanomolar range), they are not extraordinarily potent as is the case for (R)-DOI. Based upon the affinity (a measure of how tightly a particular molecule attaches to its protein target) of (R)-DOI for the receptor (Affinity=Ki=0.5 nM), and potency (a term relating to how much of a drug is necessary to produce a half maximal response) of (R)-DOI in standard pharmacological assays that measure activity of the $5\text{-HT}_{2A}$ receptor (e.g. phosphoinositide turnover; $EC_{50}$=~10-20 nM), which are similar to the affinity and potency values of other known $5\text{-HT}_{2A}$ receptor agonists including 2C-BCB and LSD, the extreme potency of (R)-DOI in blocking TNF-α mediated inflammation with an $IC_{50}$ of ~20 picomolar, about 1000 times less than is necessary to produce a half maximal effect in standard pharmacological measures of $5\text{-HT}_{2A}$ receptor activity, is unpredicted and unexpected.

EXAMPLE 5

$5\text{-HT}_{2A}$ Receptor Mediated Inhibition of TNF-α Induced Proinflammatory Marker Expression Involves Protein Kinase C (PKC)

Figure 4:
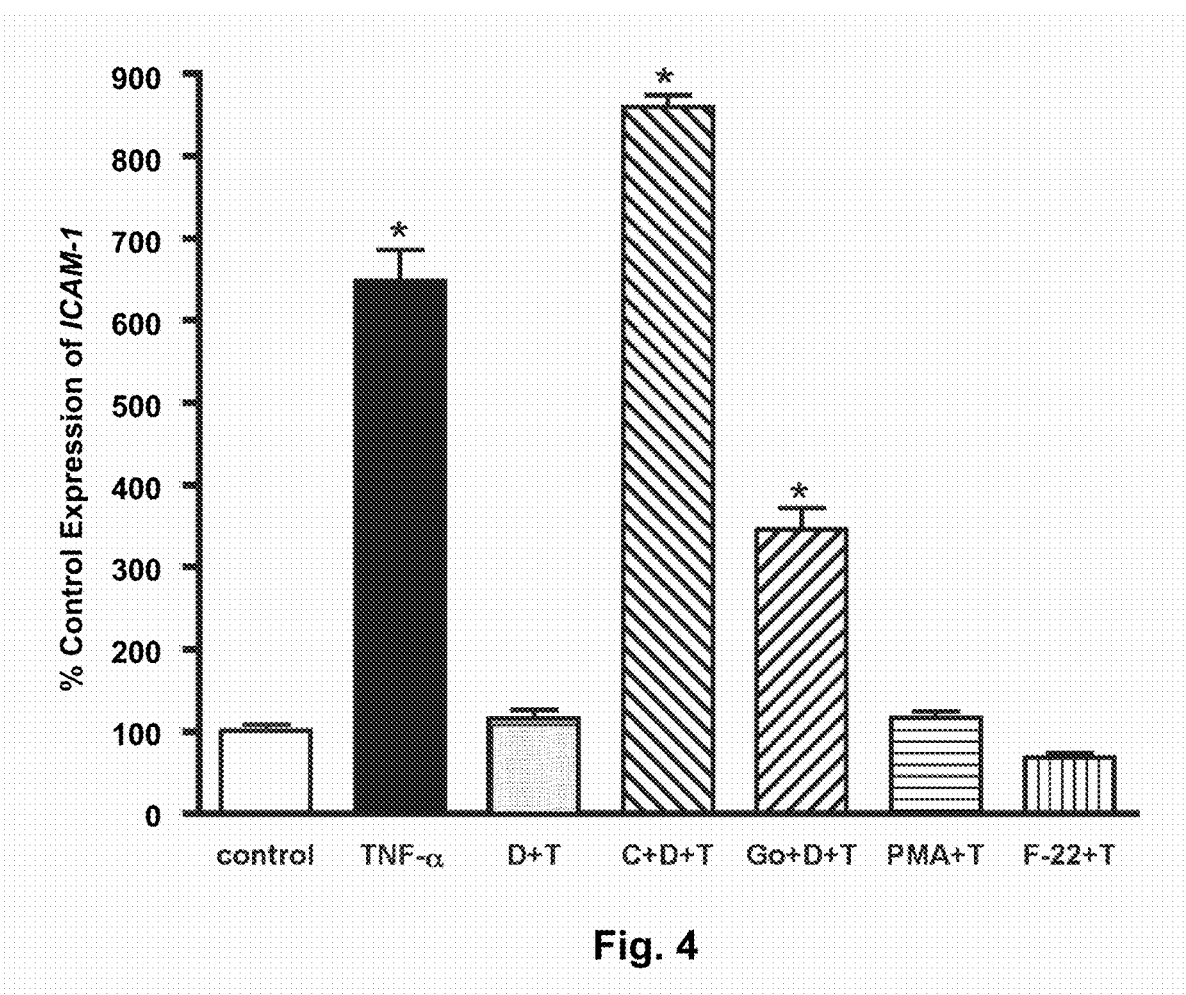
FIG. 4 illustrates the effect of 5-HT$_{2A}$ receptor activation on the expression o ICAM-1 in primary rat aortic smooth muscle cells (passage 4) under various conditions: control; TNF-α treatment alone (10 ng/ml) (TNF-α); pretreatment with (R)-DOI (1 nM, a 5-HT$_{2A}$ receptor agonist) prior to TNF-α (D+T), pretreatment with the pan-PKC isoform inhibitor chelerythrine (100 nM) for 30 minutes prior to the addition of (R)-DOI (1 nM) prior to TNF-α (C+D+T); pretreatment with the classical PKC isoform inhibitor Gö6976 (100 nM) for 30 minutes prior to the addition of (R)-DOI (1 nM) prior to TNF-α (Go+D+T); pretreatment with a PKC activator PMA (100 nM) prior to TNF-α (PMA+T); and pretreatment with a PKA inhibitor F-22 amide (100 nM) for 30 minutes prior to the addition of (R)-DOI (1 nM) prior to TNF-α (F-22+D+T). (*=p<0.01 vs control; ANOVA with Tukey post hoc).

It has been well established that ICAM-1 gene expression can be induced through pathways involving protein kinase C (PKC) (Roebuck and Finnegan, 1999). Furthermore, PKC can be activated through $5\text{-HT}_{2A}$ receptor stimulation (Roth et al., 1986). To delineate the role of PKC, RASM cells were pretreated with several chemicals prior to treatment with (R)-DOI (1 nM) and TNF-α, and then measured for ICAM-1, VCAM-1, and IL-6 gene expression. The results were identical for all three genes, and the results for ICAM-1 are shown in FIG. 4. The results for the other two genes are not shown.

The ICAM-1 gene expression was first measured using a control solution (control), only TNF-α (TNF-α), and pretreatment with (R)-DOI prior to TNF-α (D+T). Pretreatment with the pan-PKC isoform inhibitor chelerythrine (100 nM) for 30 minutes prior to the addition of (R)-DOI (1 nM) blocked the effects of TNF-α-induced gene expression for ICAM1 (C+D+T). Pretreatment with the classical PKC isoform inhibitor Gö6976 (100 nM) (Go+D+T) only blocked about 50% of the effects of (R)-DOI (1 nM) on TNF-α-induced proinflammatory gene expression, indicating that more than one PKC isoform, at least one from each class, is mediating the anti-inflammatory effects of $5\text{-HT}_{2A}$ receptor stimulation. Activation of PKC with PMA (100 nM) in the absence of (R)-DOI also blocks the effects of TNF-α (PMA+T). Inhibition of PKA with F-22 amide (100 nM) had no effect (F-22+D+T). In FIG. 4, the symbol * represent *=p<0.01 vs control; as analyzed with ANOVA with Tukey post hoc. The effects of these PKC inhibitors were the same for VCAM1 and IL6 gene expression (Data not shown). Together, these data indicate that the $5\text{-HT}_{2A}$ receptor-mediated inhibitory effects on proinflammatory gene expression are mediated through stimulation of PKC.

Thus, a pan-PKC isoform inhibitor, chelerythrine (100 nM), completely inhibited the effects of 1 nM (R)-DOI on TNF-α-induced ICAM-1 gene expression (FIG. 4), indicating that PKC plays a critical role in the mechanism of action of $5\text{-HT}_{2A}$ receptor-mediated inhibition of proinflammatory markers. To further delineate the role of specific isoforms of PKC in this process, RASM cells were pretreated with the conventional isoform inhibitor Gö6976 (100 nM) and tested the ability of (R)-DOI to inhibit TNF-α-induced proinflammatory marker expression. Only 50% of the effect of (R)-DOI was blocked, indicating that $5\text{-HT}_{2A}$ receptor stimulated anti-inflammatory effects are mediated through at least two isoforms of PKC: one conventional, and one non-conventional (FIG. 4). Finally, the ability of exogenous activation of PKC was examined using Phorbol 12-myristate 13-acetate (PMA) in RASM cells to block the effects of TNF-α on proinflammatory marker expression. In the absence of (R)-DOI, PMA (100 nM) was found to completely block TNF-α mediated expression of ICAM1, VCAM1, and IL6 (FIG. 4, results for ICAM1. Data are not shown for VCAM1 and IL6). If the effects are completely mediated through PKC, inhibiting other GPCR initiated effector pathways like PKA would have no effect. Indeed, when the effects of blocking PKA with the inhibitor F-22 amide (100 nM) was tested on the ability of (R)-DOI to block TNF-α on proinflammatory marker expression, no effect was observed (FIG. 4).

EXAMPLE 6

Effects of (R)-DOI at Blocking Proinflammatory Gene Expression is Rapid, and Present Many Hours after Addition of TNF-α

The initial dose response experiments examined the effects of 24 hour pretreatment with (R)-DOI. To determine whether this length of pretreatment was necessary to block the effects of TNF-α, a time course analysis was performed to examine the ability of (R)-DOI (1 nM) to block the effects of TNF-α (10 ng/ml) on ICAM-1 gene expression with 24 hour and one hour pretreatments, simultaneous treatment, and various time points after treatment with TNF-α. The 24 hour and one hour pretreatments, and simultaneous treatment with (R)-DOI completely blocked the effects of TNF-α (Data not shown). These data indicated that (R)-DOI very rapidly blocks proinflammatory marker expression.

Figure 5:
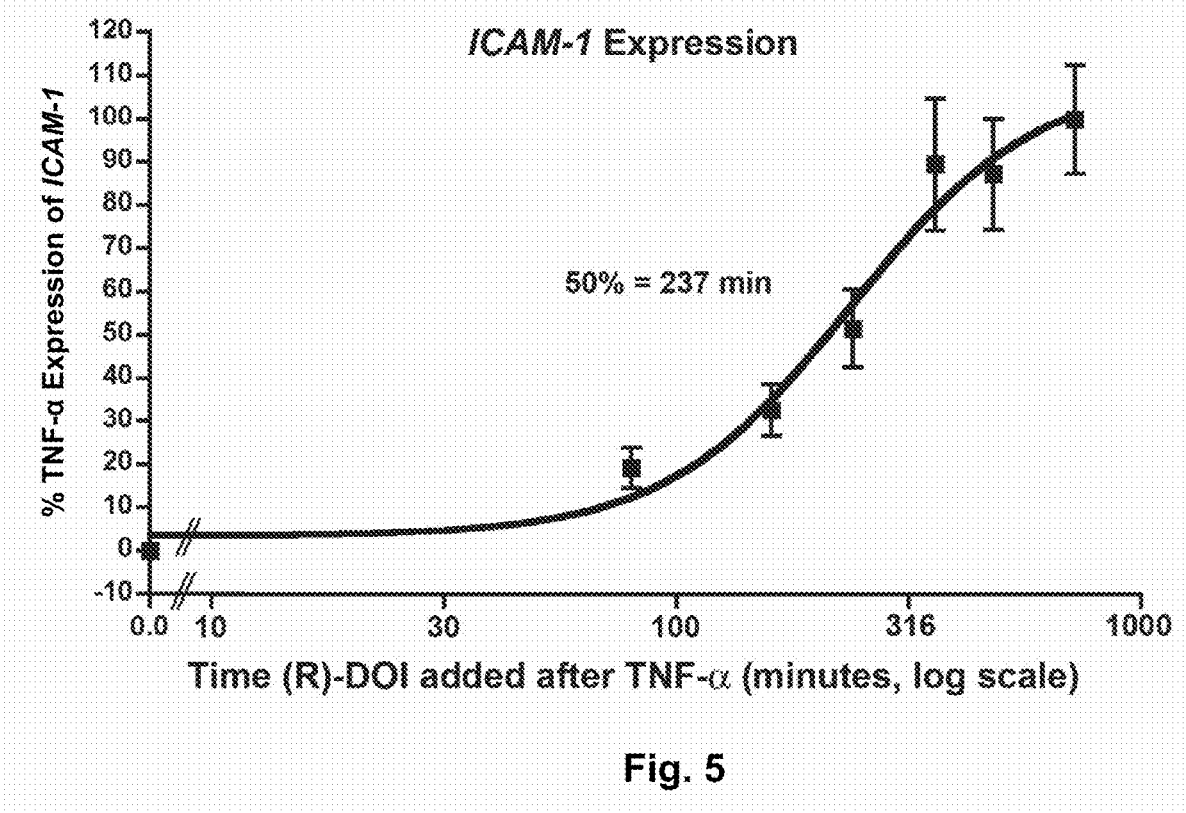
FIG. 5 illustrates a time course study examining 5-HT$_{2A}$ receptor simulation by (R)-DOI (1 nM) and its effect in inhibiting TNF-α induced ICAM1 expression when given at various time intervals after addition of TNF-α (10 ng/ml) (in minutes) in primary rat aortic smooth muscle cells (passage 4).

FIG. 5 shows a time course study examining when $5\text{-HT}_{2A}$ receptor stimulation is necessary to inhibit TNF-α-induced ICAM1 expression in RASM cells. (R)-DOI (1 nM) can block TNF-α-induced proinflammatory gene expression after addition of TNF-α (10 ng/ml) with a half maximal effect at 4 hours. Significantly, the addition of (R)-DOI after TNF-α treatment substantially blocked ICAM-1 expression with a 50% effect at about 4 hours (FIG. 5).

The activation of $5\text{-HT}_{2A}$ receptors by (R)-DOI blocks not only the effects of TNF-α when added as a pre- or co-treatment, but also when added many hours after TNF-α treatment with a half maximal effect at 4 hours post-TNF-α.

EXAMPLE 7

Nitric Oxide Synthase (NOS) Activity is Inhibited by $5\text{-HT}_{2A}$ Receptor Activation with (R)-DOI A key participant in inflammatory processes is NOS activity (Guzik et al., 2003). NOS activity can regulate NF-kB activation (Ckless et al., 2007), and cytokine pathway-activated NF-kB can transcriptionally regulate iNOS gene expression (Guo et al., 2007). To examine the effects of 5-HT$_{2A}$ receptor activation on this component of inflammatory mechanisms, primary RASM cells were used to examine the ability of 1 nM (R)-DOI to block TNF-α mediated increases in nitrite levels.

Figure 6:
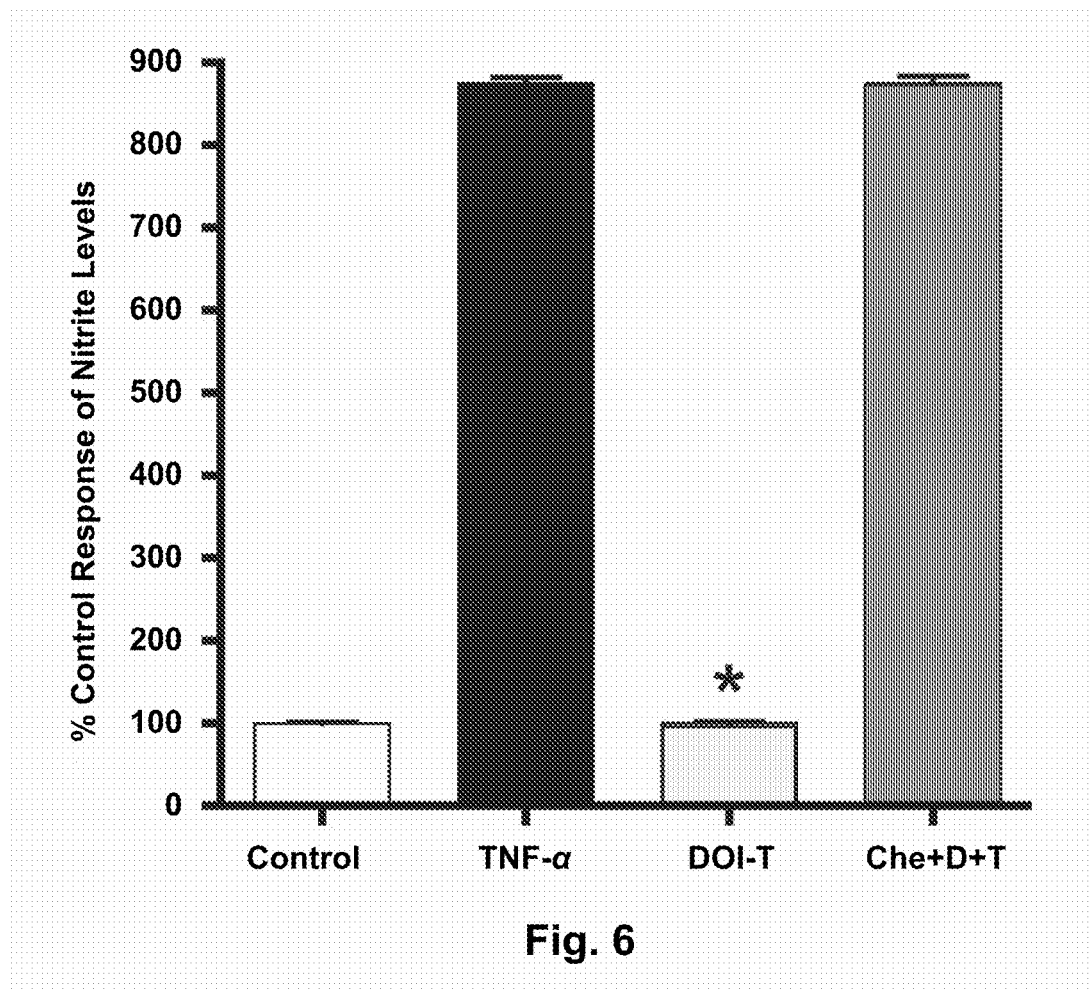
FIG. 6 illustrates the effect of 5-HT$_{2A}$ receptor activation on the levels of nitrite (an indicator of NOS activity) in primary rat aortic smooth muscle cells (passage 4) under various conditions: control; TNF-α treatment alone (10 ng/ml) (TNF-α); pretreatment with (R)-DOI (1 nM) prior to TNF-α (DOI+T), and pretreatment with the pan-PKC isoform inhibitor chelerythrine (100 nM) 30 mins prior to pretreatment with (R)-DOI (1 nM) prior to TNF-α (Che+D+T) (*=p<0.01 vs. TNF-α; ANOVA with Tukey post hoc).

As an indicator of NOS activity, nitrite levels were measured in the cell culture media after treatments and are shown in FIG. 6 as % control. TNF-α treatment (10 ng/ml) for 24 hours significantly increased nitrite levels eight-fold, indicating increased NOS activity. Pretreatment with 1 nM (R)-DOI for 24 hours blocked TNF-α mediated increases in nitrite accumulation (DOI+T). Pretreatment with the pan-PKC isoform inhibitor chelerythrine (100 nM) completely inhibited the effects of (R)-DOI (Che+D+T) (*=p<0.01 vs. TNF-α; ANOVA with Tukey post hoc). These results indicate that PKC activation is upstream of NOS activity.

EXAMPLE 8

Figure 7A:
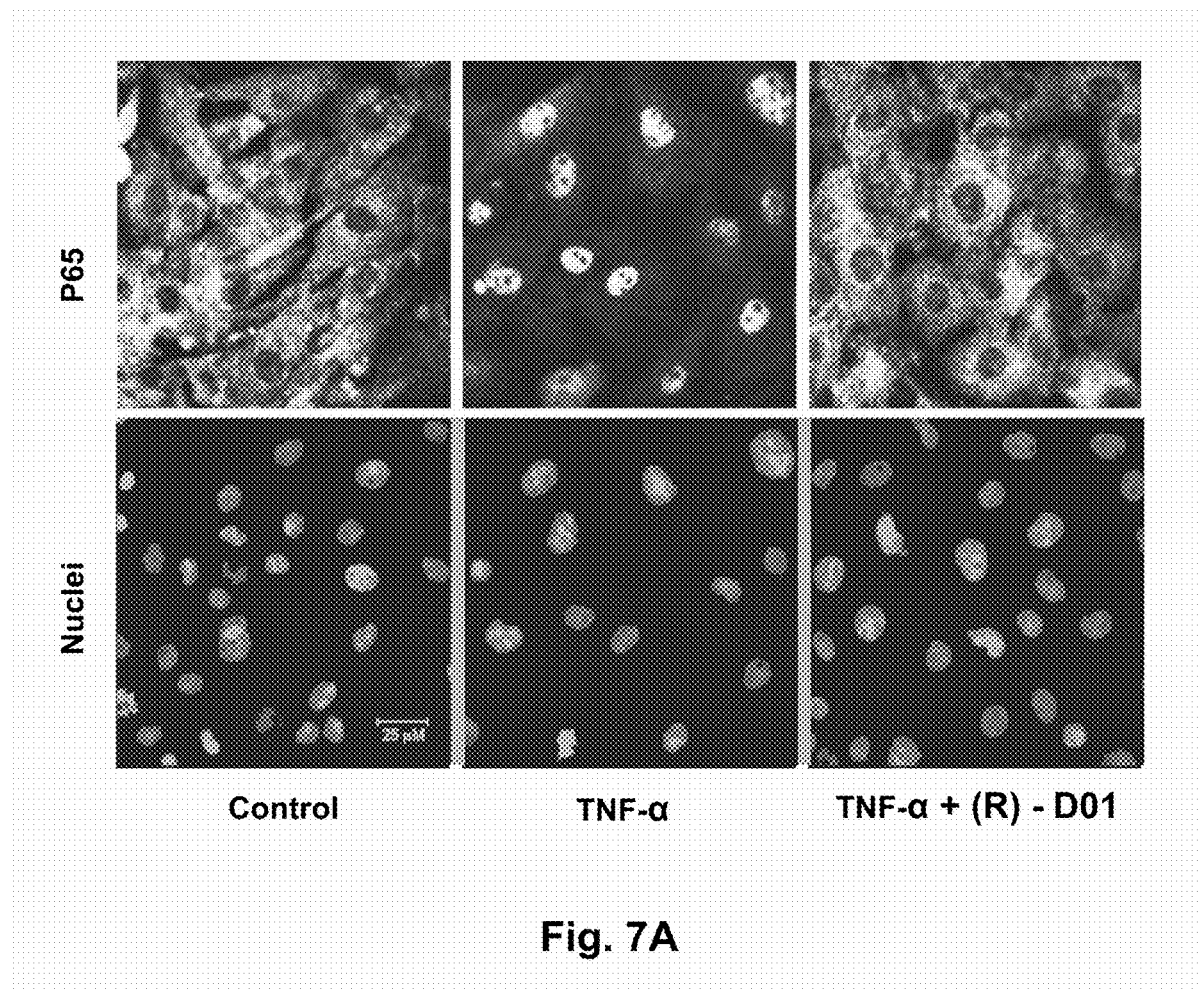
FIG. 7A illustrates both the p65 localization as visualized with Alexafluor 48 conjugated secondary antibody (the top row), and the position of the nuclei as visualized with DAPI (the bottom row) in primary rat aortic smooth muscle cells (passage 4) under various conditions: control; TNF-α treatment alone (10 ng/ml) (TNF-α); and pretreatment with (R)-DOI (1 nM) prior to TNF-α (TNF-α+(R)-DOI).
Figure 7B:
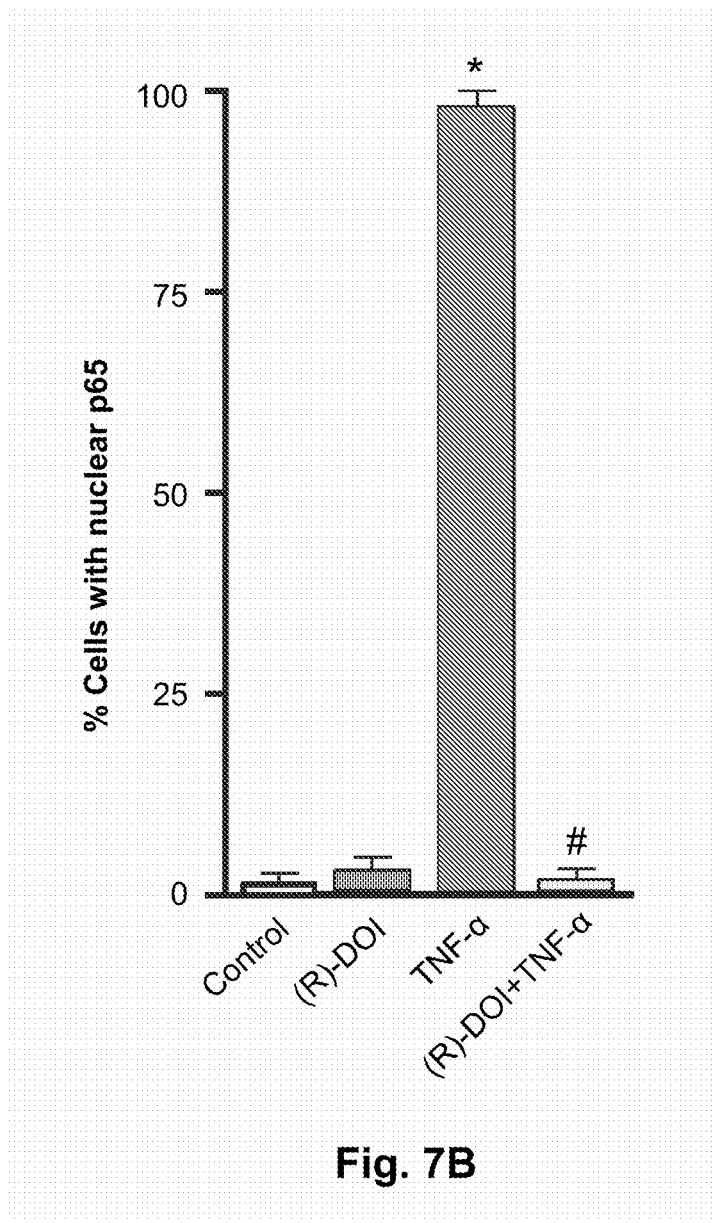
FIG. 7B illustrates the percentage of cells within a given field that predominantly showed p65 located in the nucleus under various conditions: control; (R)-DOI alone (1 nM); TNF-α treatment alone (10 ng/ml) (TNF-α); and pretreatment with (R)-DOI (1 nM) prior to TNF-α ((R)-DOI+TNF-α). (Average of three fields for each treatment; *p<0.01 vs. control, #p 0.01 vs TNF-α, ANOVA with Tukey post hoc).

Nuclear Translocation of the Activated NF-κB Subunit p65 is Blocked by 5-HT$_{2a}$ Receptor Activation with (R)-DOI Both ICAM-1 and VCAM-1 gene transcription during inflammatory processes is regulated by the transcription factor NF-κB (Collins et al., 1995). During this process, NF-κB must be activated, and then translocated from the cytoplasm to the nucleus, where it promotes gene transcription. To investigate whether 5-HT$_{2A}$ receptor stimulated inhibition of NF-κB activation and translocation might be a possible mechanism for blockade of proinflammatory gene expression changes, a series of immunohistochemical experiments were conducted examining p65 translocation in RASM cells. TNF-α treatment for 30 minutes caused the expected dramatic shift in localization of the p65 subunit of NF-κB from the cytoplasm to the nucleus (FIG. 7A). Pretreatment with 1 nM (R)-DOI for 24 hours (not shown), one hour, and together (not shown) with TNF-α (10 ng/ml) completely blocked p65 nuclear translocation (FIG. 7B). FIG. 7B shows the percentage of cells within a given field that predominantly had p65 located in the nucleus. Furthermore, pretreatment of the 1 hour time point with the PKC inhibitor chelerythrine blocked the (R)-DOI induced inhibition of p65 translocation (not shown), indicating that PKC activation is upstream of this process. The ability of (R)-DOI to block translocation when administered simultaneously with TNF-α, and not as a pretreatment, is in agreement with the above time course gene expression studies, and further supports that the effects of 5-HT$_{2A}$ receptor stimulation on inhibiting inflammatory processes are very rapid.

EXAMPLE 9

5-HT$_{2A}$ Receptor Activation Potently Blocks Proinflammatory Marker Expression in Different Cell Types Experiments were conducted to analyze for the effect of 5-HT$_{2A}$ receptor activation on proinflammatory marker expression in other cell types. Human neuroblastoma cells (SHSY5Y) and rat glioma cells (C6) can be obtained from the American Type Culture Collection (Manassas, Va.), but were provided Purdue University. The cells were grown in DMEM+10% FBS. DMEM was made and provided by the Cell and Molecular Core of the Mentoring in Cardiovascular Biology COBRE center at LSUHSC-NO. FBS was purchased from Invitrogen (Carlsbad, Calif.). Primary rat aortic endothelial cells were prepared fresh and provided by the Cell and Molecular Core of the Mentoring in Cardiovascular Biology COBRE center at LSUHSC-NO. Cells were tested at passages 3-4. Cells were grown in endothelial cell growth medium (Cell Applications, Inc.). Primary rat bronchoaveolar macrophage cells were obtained by lung lavage from rats and used at day 3 or 4 post plating in DMEM+10% FBS.

All treatments with 5-HT$_{2A}$ receptor agonists occurred 1 hour prior to the addition of TNF-alpha (10 ng/ml) or LPS (100 ng or 1 mg) depending on the experiment. All RNA isolations, cDNA synthesis, QPCR gene expression assays examining ICAM1, VCAM1, and IL6, and data analysis were performed as described above in Example 1, except the primers were different for the human cell experiment. The human gene PCR primer sequences and universal probe numbers were as follows: cyclophillin (control amplicon; Probe U64): forward primer, 5'-CCCAGTTCTTCATCAC-GACA-3' (SEQ ID NO: 11), reverse primer, 5'-GTCTTG-GTGCTCTCCACCTT-3' (SEQ ID NO: 12); and human ICAM-1 (Probe U71, intracellular adhesion molecule 1): forward primer, 5'-CCTTCCTCACCGTGTACTGG-3' (SEQ ID NO: 13), reverse primer, 5'-AGCGTAGGG-TAAGGTTCTTGC-3' (SEQ ID NO: 14).

Figure 8:
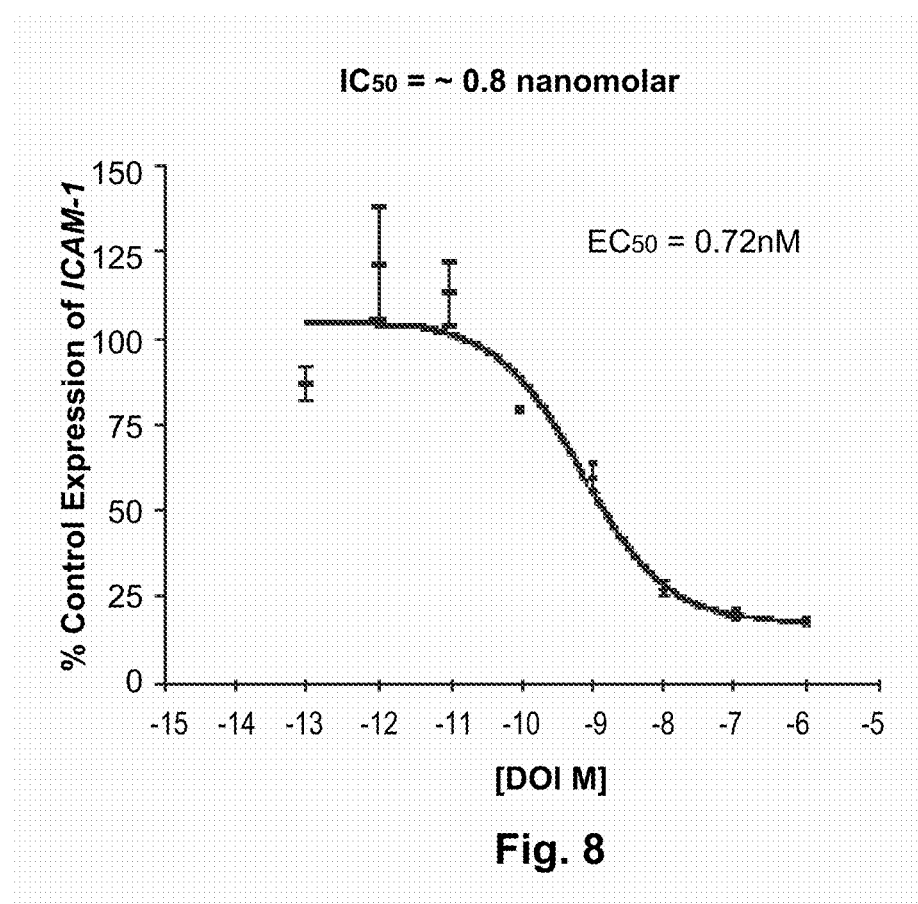
FIG. 8 illustrates the effect of 5-HT$_{2A}$ receptor activation with the agonist ( )-DOI on the expression of ICAM-1 in human neuroblastoma cells. The Y-axis represents percent of TNF-α control induction for the dose of (R)-DOI indicated on the X-axis. The IC$_{50}$ for proinflammatory gene expression inhibition for ICAM-1 is about 0.8 nM.
Figure 9:
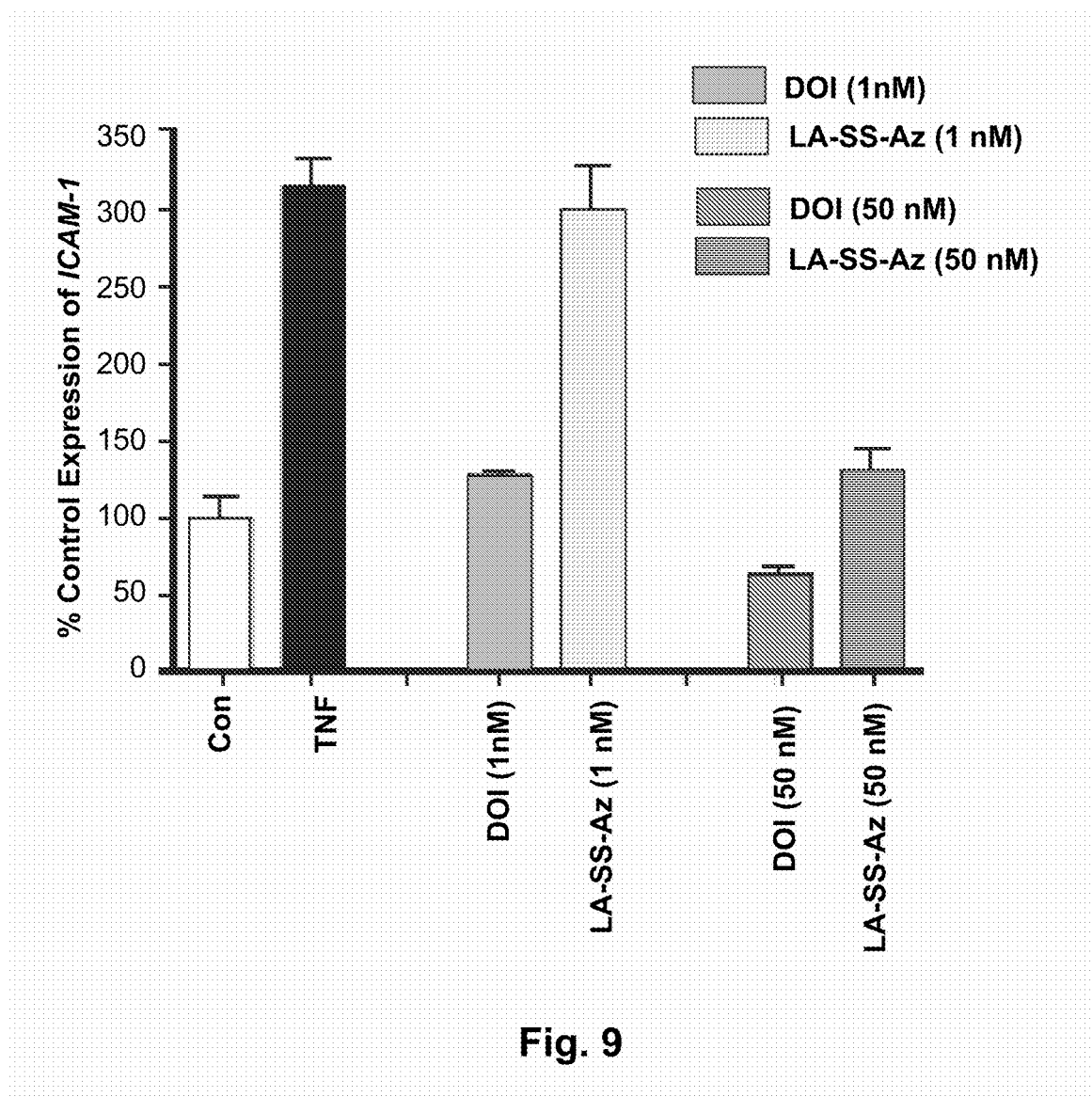
FIG. 9 illustrates the effect of 5-HT$_{2A}$ receptor activation on the expression of ICAM-1 in rat C6 glioma cells under various conditions: control; TNF-α treatment alone (10 ng/ml) (TNF); pretreatment with (R)-DOI (1 nM and 50 nM, a 5-HT$_{2A}$ receptor agonist) prior to TNF-α (DOI), and pretreatment with the indolealkylamine LA-SS-Az (1 nM and 50 nM, a 5-HT$_{2A}$ receptor agonist) prior to TNF-α (LA-SS-Az).

As shown in FIG. 8, 5-HT$_{2A}$ receptor activation with (R)-DOI blocked ICAM-1 gene expression in human neuroblastoma cells similar to results seen in RASM cells. As shown in FIG. 9, 5-HT$_{2A}$ receptor activation with (R)-DOI and LA-SS-Az in rat glioma cells blocked ICAM-1 gene expression similar to results seen in RASM cells.

Figure 10:
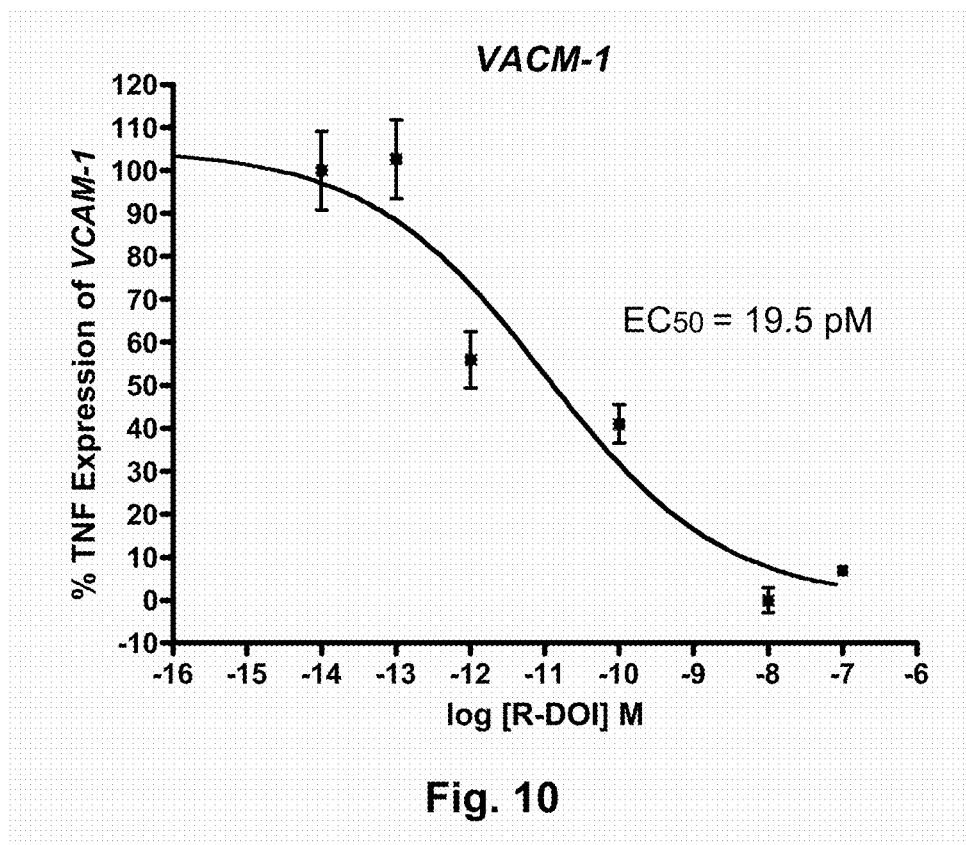
FIG. 10 illustrates the effect of 5-HT$_{2A}$ receptor activation with the agonist ( )-DOI on the expression of VCAM-1 in primary rat bronchoaveolar macrophage cells. The Y-axis represents percent of TNF-α control induction for the dose of (R)-DOI indicated on the X-axis. The IC$_{50}$ for proinflammatory gene expression inhibition for VCAM-1 is about 20 pM.

As shown in FIG. 10, (R)-DOI potently blocked VCAM-1 gene expression in response to TNF-α in primary rat bronchoaveolar macrophage cells similar to results seen in RASM cells. The IC50 was about 20 pM.

Figure 11A:
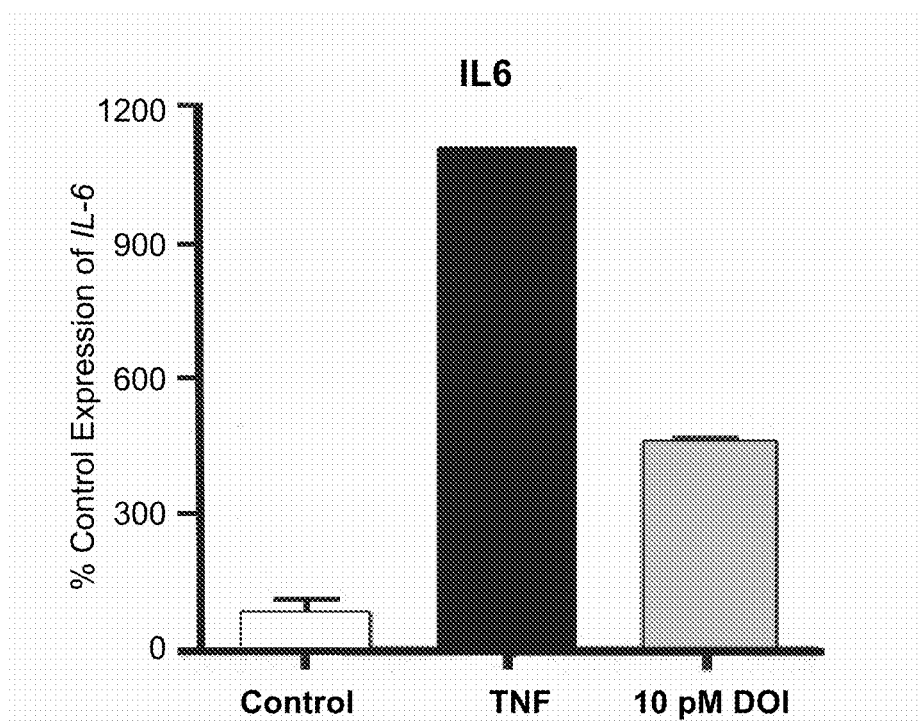
FIG. 11A illustrates the effect of 5-HT$_{2A}$ receptor activation on the expression of IL-6 in rat primary aortic endothelial cells under various conditions: control; TNF-α treatment alone (10 ng/ml) (TNF); and pretreatment with (R)-DOI (10 pM, a 5-HT$_{2A}$ receptor agonist) 60 minutes prior to TNF-α (DOI).
Figure 11B:
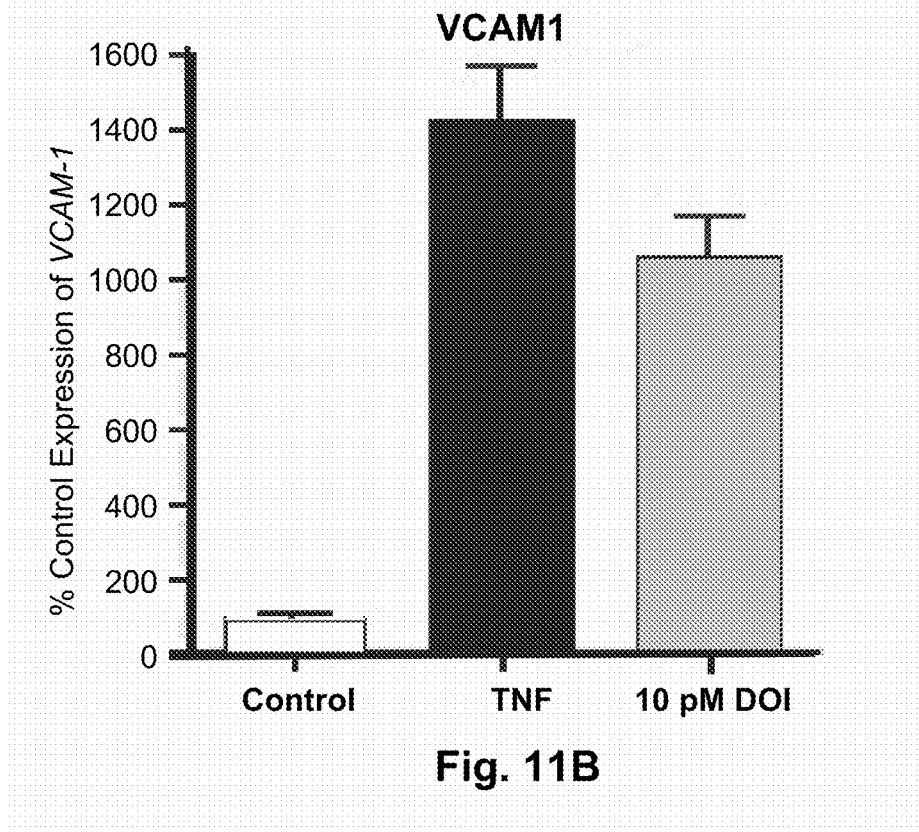
FIG. 11B illustrates the effect of 5-HT$_{2A}$ receptor activation on the expression of VCAM-1 in rat primary aortic endothelial cells under various conditions: control; TNF-α treatment alone (10 ng/ml) (TNF); and pretreatment with (R)-DOI (10 pM, a 5-HT$_{2A}$ receptor agonist) 60 minutes prior to TNF-α (DOI).

As shown in FIG. 11A, 5-HT$_{2A}$ receptor stimulation with (R)-DOI (10 pM) administered 60 minutes prior to the addition of TNF-alpha (10 ng/ml) potently inhibited TNF-α-induced IL-6 expression in rat primary aortic endothelial cells. However, the effect at inhibiting the TNF-alpha induced increase in VCAM-1 gene expression, was less potent (FIG. 11B).

Thus (R)-DOI was shown to inhibit proinflammatory gene expression in other types of cells, including human cells.

EXAMPLE 10

Figure 12:
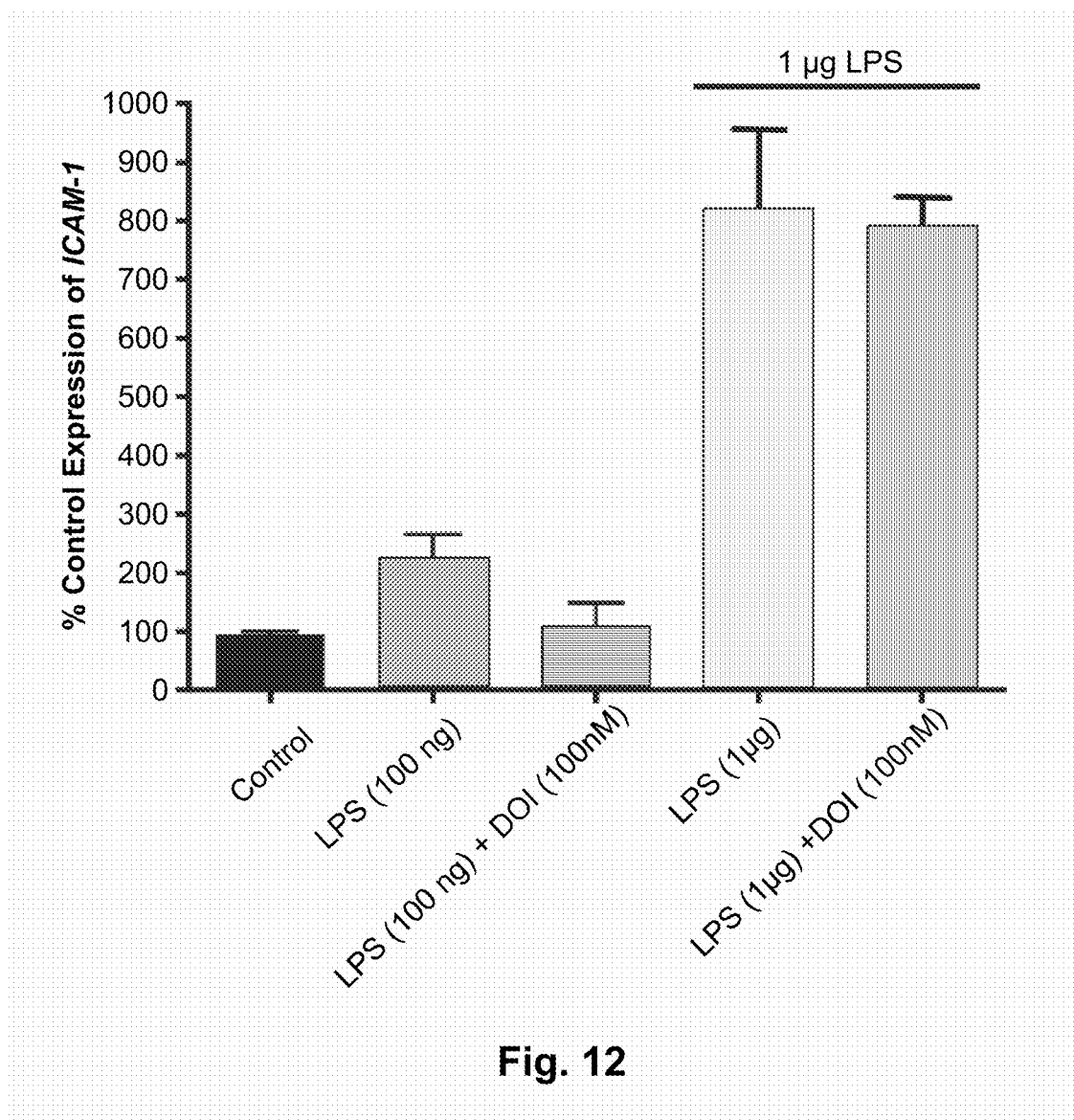
FIG. 12 illustrates the effect of 5-HT$_{2A}$ receptor activation on the expression of ICAM-1 due to stimulation with lipopolysaccharide (LPS, 100 ng and 1 µg) in primary rat aortic smooth muscle cells (passage 4) under various conditions: control; LPS treatment alone (100 ng and 1 µg); pretreatment with (R)-DOI (100 nM, a 5-HT$_{2A}$ receptor agonist) prior to LPS treatment (LPS+DOI).

5-HT$_{2A}$ Receptor Activation on ICAM-1 Gene Expression after Stimulation with Lipopolysaccharide The effect of (R)-DOI (60 minute pretreatment) on the expression of ICAM-1 in primary rat aortic smooth muscle cells after stimulation with LPS was examined. As shown in FIG. 12, at a low dose of LPS (100 ng) producing only 2-fold induction of ICAM-1 gene expression, (R)-DOT was able to block the response. At a higher dose of LPS (1 µg), there was no effect of (R)-DOI on the increase in ICAM-1. Together, these data indicate that whereas there may be a moderate effect on low levels of LPS stimulation, by and large there is little to no effect of 5-HT$_{2A}$ receptor stimulation on inflammation induced by LPS, indicating that the anti-inflammatory effects of 5-HT$_{2A}$ receptor activity are specific for the TNF-α receptor activated inflammatory mechanisms.

These results indicate that activation of 5-HT$_{2A}$ receptors by (R)-DOI, as well as additional 5-HT$_{2A}$ receptor agonists, represents an extremely potent, therapeutic avenue to explore for the treatment of diseases and disorders involving TNF-α-mediated inflammation. TNF-α and TNF-α receptor mediated pathways are believed to be a major component of many inflammatory conditions that include atherosclerosis, rheumatoid arthritis, psoriasis, type II diabetes, asthma, Crohn's Disease, inflammatory bowel syndrome, depression, schizophrenia, and Alzheimer's disease. Notably, 5-HT$_{2A}$ receptor expression has been detected in most, if not all, of the tissues mediating the inflammatory conditions mentioned above. Given the unprecedented and extremely high potency of (R)-DOI to suppress multiple proinflammatory markers rapidly, ranging from NOS activity, through NF-κB translocation, to gene expression of ICAM-1, VCAM-1 and IL-6, the predicted therapeutic dose would be at least two orders of magnitude below that necessary to produce undesirable hallucinogenic side effects. Importantly, because (R)-DOI can significantly inhibit the effects of TNF-α many hours after the administration of TNF-α, potential therapies could be aimed at not only preventing inflammation, but also treating inflammation or injury that has already occurred or is ongoing.

Miscellaneous

Following successful completion of animal trials using common mammals, (R)-DOI and other 5-HT$_{2A}$ agonists will be tested in human patients with symptoms or diseases of enhanced immunological response in clinical trials conducted in compliance with applicable laws and regulations.

Specific 5-HT$_{2A}$ agonists used in the present invention may be administered to a patient by any suitable means, including oral, intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant. They may also be administered by inhalation. Although direct oral administration may cause some loss of anti-inflammatory activity, the agonists could be packaged in such a way to protect the active ingredient(s) from digestion by use of enteric coatings, capsules or other methods known in the art.

Pharmaceutically acceptable carrier preparations include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A compound in accordance with the present invention may be formulated into therapeutic compositions as pharmaceutically acceptable salts, for example a hydrochloride salt (e.g., the (R)-DOI used in the above examples). These salts include acid addition salts formed with inorganic acids, for example hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

As used herein, the term "5-HT$_{2A}$ agonists" is any compound that increases the activity of a 5-hydroxytryptamine 2A receptor. Examples of such agonists include DOI (±)-1-(2,5-dimethoxyphenyl)-2-aminopropane hydrochloride; (R)-DOI ((R)-1-(2,5-dimethoxy-4-iodophenyl)-2-aminopropane) (greater than 95% R enantiomer); LA-SS-Az (2'S, 4'S)-(+)-9,10-Didehydro-6-methylergoline-8β-(trans-2,4-dimethylazetidide); 2C-BCB (4-Bromo-3,6-dimethoxybenzocyclobuten-1-yl) methylamine; and lysergic acid diethylamide (LSD).

As used herein, an "therapeutically effective amount" of a compound is an amount, that when administered to a patient, human or animal, (whether as a single dose or as a time course of treatment) inhibits or reduces the release of proinflammatory compounds to a clinically significant degree; or alternatively, to a statistically significant degree as compared to control. "Statistical significance" means significance at the $P<0.05$ level, or such other measure of statistical significance as would be used by those of skill in the art of biomedical statistics in the context of a particular type of treatment or prophylaxis. The term "therapeutically effective amount" therefore includes, for example, an amount sufficient to decrease the release of proinflammatory compounds to a clinically relevant level that is statistically significant to decrease inflammation. The dosage ranges for the administration of a compound are those that produce the desired effect, but an effective dose that would result in the tissue cells seeing no greater than a body fluid concentration of no greater than 5 nM, more preferable no greater than 1 nM, and most preferably no greater than 0.5 nM. For example, a single dose that would result in a 1 nM final body fluid concentration in a 60 kg human would be about 20 µg, or for (R)-DOI a single dose that would result in a final body fluid concentration near the IC50 of about 20 pM would be about 0.4 µg. This amount could be adjusted based on the size of the human or animal. Generally, the dosage will vary with the age, weight, condition, and the degree of the inflammation. A person of ordinary skill in the art, given the teachings of the present specification, may readily determine suitable dosage ranges for the various sizes of different mammals. The dosage can be adjusted by the individual physician or veterinarian in the event of any contraindications. In any event, the effectiveness of treatment can be determined by monitoring the extent of release of known inflammatory parameters by methods well known to those in the field.

REFERENCES

Akiyoshi T, Zhang Q, Inoue F, Aramaki O, Hatano M, Shimazu M, Kitajima M, Shirasugi N and Niimi M (2006) Induction of indefinite survival of fully mismatched cardiac allografts and generation of regulatory cells by sarpogrelate hydrochloride. *Transplantation* 82:1051-1059.

Arzt E, Costas M, Finkielman S and Nahmod V E (1991) Serotonin inhibition of tumor necrosis factor-alpha synthesis by human monocytes. *Life Sci* 48:2557-2562.

Blankenberg S, Barbaux S and Tiret L (2003) Adhesion molecules and atherosclerosis. *Atherosclerosis* 170:191-203.

Ckless K, van der Vliet A and Janssen-Heininger Y (2007) Oxidative-nitrosative stress and post-translational protein modifications: implications to lung structure-function relations. Arginase modulates NF-kappaB activity via a nitric oxide-dependent mechanism. *Am J Respir Cell Mol Biol* 36:645-653.

Cloez-Tayarani I, Petit-Bertron A F, Venters H D and Cavaillon J M (2003) Differential effect of serotonin on cytokine production in lipopolysaccharide-stimulated human peripheral blood mononuclear cells: involvement of 5-hydroxytryptamine2A receptors. *Int Immunol* 15:233-240.

Collins T, Read M A, Neish A S, Whitley M Z, Thanos D and Maniatis T (1995) Transcriptional regulation of endothelial cell adhesion molecules: NF-kappa B and cytokine-inducible enhancers. *Faseb J* 9:899-909.

Crisafulli C, Galuppo M, and Cuzzocrea S (2009) Effects of genetic and pharmacological inhibition of TNF-alpha in the regulation of inflammation in macrophases. *Pharmacol. Res.* Epub 2009 May 18.

Dunn A J, Swiergiel A H and de Beaurepaire R (2005) Cytokines as mediators of depression: what can we learn from animal studies? *Neurosci Biobehav Rev* 29:891-909.

Guo Z, Shao L, Du Q, Park K S and Geller D A (2007) Identification of a classic cytokine-induced enhancer upstream in the human iNOS promoter. *Faseb J* 21:535-542.

Guzik T J, Korbut R and Adamek-Guzik T (2003) Nitric oxide and superoxide in inflammation and immune regulation. *J Physiol Pharmacol* 54:469-487.

Hansson G K, Robertson A K and Soderberg-Naucler C (2006) Inflammation and atherosclerosis. *Annu Rev Pathol* 1:297-329.

Hughes J M, Arthur C A, Baracho S, Carlin S M, Hawker K M, Johnson P R and Armour C L (2000) Human eosinophil-airway smooth muscle cell interactions. *Mediators Inflamm* 9:93-99.

Huntjens D R, Danhof M and Della Pasqua O E (2005) Pharmacokinetic-pharmacodynamic correlations and biomarkers in the development of COX-2 inhibitors. *Rheumatology (Oxford)* 44:846-859.

Ito T, Ikeda U, Shimpo M, Yamamoto K and Shimada K (2000) Serotonin increases interleukin-6 synthesis in human vascular smooth muscle cells. *Circulation* 102:2522-2527.

Kim Y K, Jung H G, Myint A M, Kim H and Park S H (2007) Imbalance between pro-inflammatory and anti-inflammatory cytokines in bipolar disorder. *J Affect Disord* 104:91-95.

Kubera M, Maes M, Kenis G, Kim Y K and Lason W (2005) Effects of serotonin and serotonergic agonists and antagonists on the production of tumor necrosis factor alpha and interleukin-6. *Psychiatry Res* 134:251-258.

Kurrasch-Orbaugh D M, Watts V J, Barker E L and Nichols D E (2003) Serotonin 5-hydroxytryptamine 2A receptor-coupled phospholipase C and phospholipase A2 signaling pathways have different receptor reserves. *J Pharmacol Exp Ther* 304:229-237.

Little K Y, Elmer L W, Zhong H, Scheys J O and Zhang L (2002) Cocaine induction of dopamine transporter trafficking to the plasma membrane. *Mol Pharmacol* 61:436-445.

Marconi A, Darquenne S, Boulmerka A, Mosnier M and D'Alessio P (2003) Naftidrofuryl-driven regulation of endothelial ICAM-1 involves nitric oxide. *Free Radic Biol Med* 34:616-625.

McLean T H, Parrish J C, Braden M R, Marona-Lewicka D, Gallardo-Godoy A and Nichols D E (2006) 1-Aminomethylbenzocycloalkanes: conformationally restricted hallucinogenic phenethylamine analogues as functionally selective 5-HT2A receptor agonists. *J Med Chem* 49:5794-5803.

Miller K J and Gonzalez H A (1998) Serotonin 5-HT2A receptor activation inhibits cytokine-stimulated inducible nitric oxide synthase in C6 glioma cells. *Ann N Y Acad Sci* 861:169-173.

Miller K J, Mariano C L and Cruz W R (1997) Serotonin 5HT2A receptor activation inhibits inducible nitric oxide synthase activity in C6 glioma cells. *Life Sci* 61:1819-1827.

Nagatomo T, Rashid M, Abul Muntasir H and Komiyama T (2004) Functions of 5-HT2A receptor and its antagonists in the cardiovascular system. *Pharmacol Ther* 104:59-81.

Nichols D E (2004) Hallucinogens. *Pharmacol Ther* 101:131-181.

Nichols D E, Frescas S, Marona-Lewicka D and Kurrasch-Orbaugh D M (2002) Lysergamides of isomeric 2,4-dimethylazetidines map the binding orientation of the diethylamide moiety in the potent hallucinogenic agent N,N-diethyllysergamide (LSD). *J Med Chem* 45:4344-4349.

Nichols D E and Nichols C D (2008) Serotonin Receptors. *Chem. Rev* 108:1614-1641.

Popa C, Netea M G, van Riel P L, van der Meer J W and Stalenhoef A F (2007) The role of TNF-alpha in chronic inflammatory conditions, intermediary metabolism, and cardiovascular risk. *J Lipid Res* 48:751-762.

Reimold A M (2002) TNFalpha as therapeutic target: new drugs, more applications. *Curr Drug Targets Inflamm Allergy* 1:377-392.

Roebuck K A and Finnegan A (1999) Regulation of intercellular adhesion molecule-1 (CD54) gene expression. *J Leukoc Biol* 66:876-888.

Roth B L and Chuang D M (1987) Multiple mechanisms of serotonergic signal transduction. *Life Sci* 41:1051-1064.

Roth B L, Nakaki T, Chuang D M and Costa E (1986) 5-Hydroxytryptamine2 receptors coupled to phospholipase C in rat aorta: modulation of phosphoinositide turnover by phorbol ester. *J Pharmacol Exp Ther* 238:480-485.

Saetre P, Emilsson L, Axelsson E, Kreuger J, Lindholm E and Jazin E (2007) Inflammation-related genes up-regulated in schizophrenia brains. *BMC Psychiatry* 7:46.

Saucier C, Morris S J and Albert P R (1998) Endogenous serotonin-2A and -2C receptors in Balb/c-3T3 cells revealed in serotonin-free medium: desensitization and down-regulation by serotonin. *Biochem Pharmacol* 56:1347-1357.

Shulgin A and Shulgin A (1991) *PiHKAL*. Transform Press, Berkeley.

Stefulj J, Jernej B, Cicin-Sain L, Rinner I and Schauenstein K (2000) mRNA expression of serotonin receptors in cells of the immune tissues of the rat. *Brain Behav Immun* 14:219-224.

Tracey D, Klareskog L, Sasso E H, Salfeld J G and Tak P P (2007) Tumor necrosis factor antagonist mechanisms of action: A comprehensive review. *Pharmacol Ther.*

Tweedie D, Sambamurti K and Greig N H (2007) TNF-alpha inhibition as a treatment strategy for neurodegenerative disorders: new drug candidates and targets. *Curr Alzheimer Res* 4:378-385.

Urban J D, Clarke W P, von Zastrow M, Nichols D E, Kobilka B, Weinstein H, Javitch J A, Roth B L, Christopoulos A, Sexton P M, Miller K J, Spedding M and Mailman R B (2007) Functional selectivity and classical concepts of quantitative pharmacology. *J Pharmacol Exp Ther* 320:1-13.

Williams R O, Paleolog E and Feldmann M (2007) Cytokine inhibitors in rheumatoid arthritis and other autoimmune diseases. *Curr Opin Pharmacol* 7:412-417.

Willins D L, Deutch A Y and Roth B L (1997) Serotonin 5-HT2A receptors are expressed on pyramidal cells and interneurons in the rat cortex. *Synapse* 27:79.

Zerfaoui M, Suzuki Y, Naura A S, Hans C P, Nichols C and Boulares A H (2008) Nuclear translocation of p65 NF-kappaB is sufficient for VCAM-1, but not ICAM-1, expression in TNF-stimulated smooth muscle cells: Differential requirement for PARP-1 expression and interaction. *Cell Signal* 20:186-194.

---

We claim:

1. A method for the treatment of an inflammatory disorder in a mammal, said method comprising administering to a mammal in need of such treatment a therapeutically effective amount of (R)-1-(2,5-dimethoxy-4-iodophenyl)-2-aminopropane ((R)-DOI) in a pharmaceutically acceptable carrier or salt thereof, wherein said inflammatory disorder is associated with a disease selected from asthma, rheumatoid arthritis, irritable bowel syndrome, and Crohn's disease.

2. The method of claim 1, wherein the ((R)-DOI) is administered in an amount sufficient to reduce the expression of the intercellular adhesion molecule 1 (ICAM-1) gene associated with stimulation of the tumor necrosis factor-alpha receptor (TNF-α).

3. The method of claim 2, wherein the inflammatory disorder is asthma.

4. The method of claim 2, wherein the inflammatory disorder is rheumatoid arthritis.

5. The method of claim 2, wherein the inflammatory disorder is irritable bowel syndrome.

6. The method of claim 2, wherein the inflammatory disorder is Crohn's disease.

7. The method of claim 1, wherein the mammal is a human.

* * * * *

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial sequence
<220> FEATURE:
<223> OTHER INFORMATION: Synthetic

<400> SEQUENCE: 1
tgatgtcact tgccatagct g                                                  21

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
tcgcacagag cttgctagg                                                     19

<210> SEQ ID NO 3
<211> LENGTH: 20
<212> TYPE: DNA
<213> ORGANISM: Artificial sequence
<220> FEATURE:
<223> OTHER INFORMATION: Synthetic

<400> SEQUENCE: 3
ttctgccacc atcactgtgt                                                    20

<210> SEQ ID NO 4
<211> LENGTH: 19
<212> TYPE: DNA
<213> ORGANISM: Artificial sequence
<220> FEATURE:
<223> OTHER INFORMATION: Synthetic

<400> SEQUENCE: 4
agcgcaggat gaggttctt                                                     19

<210> SEQ ID NO 5
<211> LENGTH: 21
<212> TYPE: DNA
<213> ORGANISM: Artificial sequence
<220> FEATURE:
<223> OTHER INFORMATION: Synthetic
```

<400> SEQUENCE: 5
caaatggagt ctgaacccaa a                                                    21

<210> SEQ ID NO 6
<211> LENGTH: 18
<212> TYPE: DNA
<213> ORGANISM: Artificial sequence
<220> FEATURE:
<223> OTHER INFORMATION: Synthetic

<400> SEQUENCE: 6
ggttctttcg gagcaacg                                                        18

<210> SEQ ID NO 7
<211> LENGTH: 23
<212> TYPE: DNA
<213> ORGANISM: Artificial sequence
<220> FEATURE:
<223> OTHER INFORMATION: Synthetic

<400> SEQUENCE: 7
cctggagttt gtgaagaaca act                                                  23

<210> SEQ ID NO 8
<211> LENGTH: 20
<212> TYPE: DNA
<213> ORGANISM: Artificial sequence
<220> FEATURE:
<223> OTHER INFORMATION: Synthetic

<400> SEQUENCE: 8
ggaagttggg gtaggaagga                                                      20

<210> SEQ ID NO 9
<211> LENGTH: 19
<212> TYPE: DNA
<213> ORGANISM: Artificial sequence
<220> FEATURE:
<223> OTHER INFORMATION: Synthetic

<400> SEQUENCE: 9
acgtggtttt cggcaaagt                                                       19

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
cttggtgttc tccaccttcc                                                      20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
cccagttctt catcacgaca                                                      20

<210> SEQ ID NO 12

```
<211> LENGTH: 20
<212> TYPE: DNA
<213> ORGANISM: Artificial sequence
<220> FEATURE:
<223> OTHER INFORMATION: Synthetic

<400> SEQUENCE: 12
gtcttggtgc tctccacctt                                          20

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
ccttcctcac cgtgtactgg                                          20

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
agcgtagggt aaggttcttg c                                        21
```